(12) United States Patent  
Sato et al.

(10) Patent No.: US 8,802,350 B2
(45) Date of Patent: Aug. 12, 2014

(54) PHOTORESIST COMPOSITION, RESIST-PATTERN FORMING METHOD, POLYMER, AND COMPOUND

(75) Inventors: Mitsuo Sato, Tokyo (JP); Masafumi Yoshida, Tokyo (JP)

(73) Assignee: JSR Corporation, Tokyo (JP)

( * ) Notice: Subject to any disclaimer, the term of this patent is extended or adjusted under 35 U.S.C. 154(b) by 30 days.

(21) Appl. No.: 13/438,868

(22) Filed: Apr. 4, 2012

(65) Prior Publication Data

US 2012/0258402 A1    Oct. 11, 2012

(30) Foreign Application Priority Data

Apr. 11, 2011    (JP) .................................. 2011-87814

(51) Int. Cl.
| | |
|---|---|
| G03F 7/00 | (2006.01) |
| C08F 118/02 | (2006.01) |
| C08F 20/28 | (2006.01) |
| C07C 69/74 | (2006.01) |

(52) U.S. Cl.
USPC ........ 430/270.1; 526/319; 526/320; 560/220; 430/322

(58) Field of Classification Search
USPC .................................. 430/326, 270.1; 526/319
See application file for complete search history.

(56) References Cited

U.S. PATENT DOCUMENTS

| | | | |
|---|---|---|---|
| 4,491,628 A | 1/1985 | Ito et al. | |
| 2003/0194640 A1* | 10/2003 | Sato ............................ | 430/270.1 |
| 2005/0277059 A1 | 12/2005 | Kanda | |
| 2009/0202945 A1 | 8/2009 | Nakagawa et al. | |
| 2009/0306328 A1* | 12/2009 | Yamagishi et al. ........... | 528/272 |
| 2010/0062372 A1* | 3/2010 | Nishi et al. .................. | 430/286.1 |
| 2010/0112475 A1* | 5/2010 | Natsume et al. ........... | 430/270.1 |

FOREIGN PATENT DOCUMENTS

| | | |
|---|---|---|
| EP | 0159428 | 10/1985 |
| JP | 59-45439 | 3/1984 |
| JP | 59-93448 | 5/1984 |
| JP | 6-12452 | 1/1994 |
| JP | 2005-352384 | 12/2005 |
| WO | WO 2007/116664 | 10/2007 |

* cited by examiner

*Primary Examiner* — Cynthia H Kelly
*Assistant Examiner* — Alyssa L Cepluch
(74) *Attorney, Agent, or Firm* — Ditthavong & Steiner, P.C.

(57) ABSTRACT

A photoresist composition includes a polymer that includes a structural unit shown by the following formula (1), and a photoacid generator. $R^1$ in the formula (1) represents a hydrogen atom, a fluorine atom, a methyl group, or a trifluoromethyl group, Z represents a group that forms a divalent alicyclic group having 3 to 20 carbon atoms together with a carbon atom bonded to X, X represents an alkanediyl group having 1 to 6 carbon atoms, Y represents a hydrogen atom or —$CR^2R^3$ ($OR^4$), and $R^2$ to $R^4$ independently represent a hydrogen atom or a monovalent hydrocarbon group, provided that $R^3$ and $R^4$ optionally bond to each other to form a cyclic ether structure together with a carbon atom bonded to $R^3$ and an oxygen atom bonded to $R^4$.

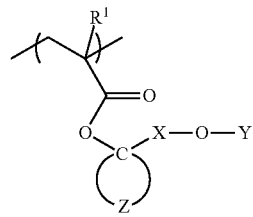

(1)

12 Claims, No Drawings

PHOTORESIST COMPOSITION, RESIST-PATTERN FORMING METHOD, POLYMER, AND COMPOUND

CROSS-REFERENCE TO RELATED APPLICATIONS

The present application claims priority under 35 U.S.C. §119 to Japanese Patent Application No. 2011-87814, filed Apr. 11, 2011. The contents of this application are incorporated herein by reference in their entirety.

BACKGROUND OF THE INVENTION

1. Field of the Invention

The invention relates to a photoresist composition, a resist pattern-forming method, a polymer, and a compound.

2. Discussion of the Background

In the field of microfabrication used to produce an integrated circuit device or the like, lithographic technology that utilizes short-wavelength radiation (e.g., KrF excimer laser light (wavelength: 248 nm) or ArF excimer laser light (wavelength: 193 nm)) has been under development in order to achieve a higher degree of integration. A resist material that exhibits high sensitivity, high resolution, and the like is required when using such an exposure light source. A chemically-amplified photoresist composition that includes an acid-labile group-containing component and an acid generator that generates an acid upon exposure to radiation has been normally used as the resist material (see Japanese Patent Application Publication (KOKAI) No. 59-45439).

In recent years, technology that utilizes radiation having a wavelength shorter than that of excimer laser light (e.g., X-rays, electron beams (EB), or extreme ultraviolet (EUV) light) has been studied along with a further increase in the degree of integration (miniaturization) of devices. However, when forming a fine resist pattern using a known photoresist composition, it is difficult to achieve sufficient lithographic performance that is indicated by a mask error enhancement factor (MEEF) (i.e., a value that indicates a mask error latitude), line width roughness (LWR) (i.e., a value that indicates a variation in line width), and the like.

In view of the above situation, a photoresist composition used to form a finer resist pattern has been required to exhibit improved basic properties (e.g., sensitivity) and improved lithographic performance (e.g., MEEF and LWR).

SUMMARY OF THE INVENTION

According to one aspect of the invention, a photoresist composition includes a polymer that includes a structural unit shown by a formula (1), and a photoacid generator.

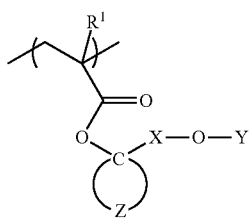

(1)

wherein $R^1$ represents a hydrogen atom, a fluorine atom, a methyl group, or a trifluoromethyl group, Z represents a group that forms a divalent alicyclic group having 3 to 20 carbon atoms together with a carbon atom bonded to X, X represents an alkanediyl group having 1 to 6 carbon atoms, Y represents a hydrogen atom or $-CR^2R^3(OR^4)$, and $R^2$ to $R^4$ independently represent a hydrogen atom or a monovalent hydrocarbon group, provided that $R^3$ and $R^4$ optionally bond to each other to form a cyclic ether structure together with a carbon atom bonded to $R^3$ and an oxygen atom bonded to $R^4$.

According to another aspect of the invention, a resist pattern-forming method includes applying the photoresist composition to a substrate to form a resist film. The resist film is exposed by applying radiation to the resist film via a photomask. The exposed resist film is heated. The heated resist film is developed.

According to another aspect of the invention, a polymer includes a structural unit shown by a formula (1).

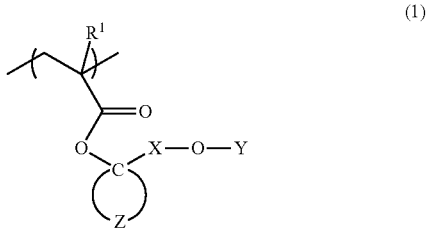

(1)

wherein $R^1$ represents a hydrogen atom, a fluorine atom, a methyl group, or a trifluoromethyl group, Z represents a group that forms a divalent alicyclic group having 3 to 20 carbon atoms together with a carbon atom bonded to X, X represents an alkanediyl group having 1 to 6 carbon atoms, Y represents a hydrogen atom or $-CR^2R^3(OR^4)$, and $R^2$ to $R^4$ independently represent a hydrogen atom or a monovalent hydrocarbon group, provided that $R^3$ and $R^4$ optionally bond to each other to form a cyclic ether structure together with a carbon atom bonded to $R^3$ and an oxygen atom bonded to $R^4$.

According to another aspect of the invention, a compound is shown by a formula (i).

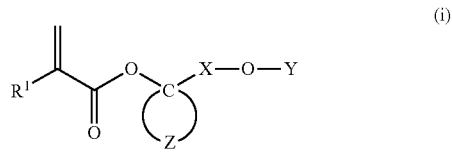

(i)

wherein $R^1$ represents a hydrogen atom, a fluorine atom, a methyl group, or a trifluoromethyl group, Z represents a group that forms a divalent alicyclic group having 3 to 20 carbon atoms together with a carbon atom bonded to X, X represents an alkanediyl group having 1 to 6 carbon atoms, Y represents a hydrogen atom or $-CR^2R^3(OR^4)$, and $R^2$ to $R^4$ independently represent a hydrogen atom or a monovalent hydrocarbon group, provided that $R^3$ and $R^4$ optionally bond to each other to form a cyclic ether structure together with a carbon atom bonded to $R^3$ and an oxygen atom bonded to $R^4$.

DESCRIPTION OF THE EMBODIMENTS

A photoresist composition according to one embodiment of the invention includes (A) a polymer that includes a structural unit shown by the following formula (1) (hereinafter may be referred to as "structural unit (I)") (hereinafter may be referred to as "polymer (A)"), and (B) a photoacid generator (hereinafter may be referred to as "acid generator (B)").

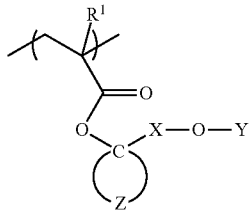

(1)

wherein $R^1$ represents a hydrogen atom, a fluorine atom, a methyl group, or a trifluoromethyl group, Z represents a group that forms a divalent alicyclic group having 3 to 20 carbon atoms together with the carbon atom bonded to X, X represents an alkanediyl group having 1 to 6 carbon atoms, Y represents a hydrogen atom or $-CR^2R^3(OR^4)$, and $R^2$ to $R^4$ independently represent a hydrogen atom or a monovalent hydrocarbon group, provided that $R^3$ and $R^4$ may bond to each other to form a cyclic ether structure together with the carbon atom bonded to $R^3$ and the oxygen atom bonded to $R^4$.

The photoresist composition includes the polymer (A) and the acid generator (B). It is considered that the acid diffusion length (hereinafter may be referred to as "diffusion length") in a resist film decreases when the photoresist composition includes the polymer (A) that includes the structural unit (I) that includes a hydroxyl group or an acetal group at the above specific position, so that the photoresist composition exhibits improved lithographic performance (e.g., MEEF and LWR), and exhibits sufficient basic properties (e.g., sensitivity).

It is preferable that X represent an alkanediyl group having 2 to 4 carbon atoms. When X included in the structural unit (I) represents an alkanediyl group having 2 to 4 carbon atoms, the photoresist composition exhibits further improved lithographic performance (e.g., MEEF and LWR).

It is preferable that Z represent a group that forms a divalent monoalicyclic group having 5 to 8 carbon atoms together with the carbon atom bonded to X. When the structural unit (I) includes a divalent monoalicyclic hydrocarbon group having 5 to 8 carbon atoms, the photoresist composition exhibits further improved lithographic performance (e.g., MEEF and LWR).

It is preferable that Y represent $-CR^2R^3(OR^4)$. When Y included in the structural unit (I) represents an acetal group having the above specific structure, the photoresist composition exhibits more excellent lithographic performance (e.g., MEEF and LWR).

The polymer (A) preferably further includes a structural unit shown by the following formula (2) (hereinafter may be referred to as "structural unit (II)").

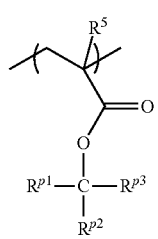

(2)

wherein $R^5$ represents a hydrogen atom, a fluorine atom, a methyl group, or a trifluoromethyl group, $R^{p1}$ represents a chain-like hydrocarbon group having 1 to 10 carbon atoms or an alicyclic group having 3 to 20 carbon atoms, and $R^{p2}$ and $R^{p3}$ independently represent a chain-like hydrocarbon group having 1 to 10 carbon atoms or an alicyclic group having 4 to 20 carbon atoms, provided that $R^{p2}$ and $R^{p3}$ may bond to each other to form a divalent alicyclic group having 4 to 20 carbon atoms together with the carbon atom bonded to $R^{p2}$ and $R^{p3}$.

When the polymer (A) further includes the structural unit (II) that includes an acid-labile group and has the above specific structure, the photoresist composition exhibits sufficient basic properties (e.g., sensitivity), and exhibits excellent lithographic performance (e.g., MEEF and LWR).

The photoresist composition preferably further includes (C) at least one compound selected from the group consisting of a compound shown by the following formula (3-1) and a compound shown by the following formula (3-2) (hereinafter may be referred to as "compound (C)").

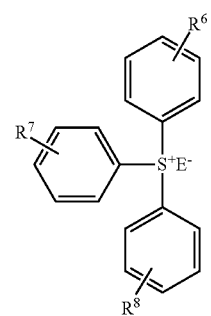

(3-1)

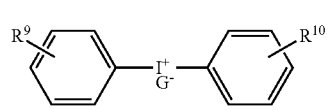

(3-2)

wherein $R^6$ to $R^{10}$ independently represent a hydrogen atom, an alkyl group, an alkoxy group, a hydroxyl group, or a halogen atom, $E^-$ and $G^-$ independently represent $OH^-$, $R^A-COO^-$, $R^A-SO_3^-$, or $R^A-N^--SO_2-R^B$, $R^A$ represents an alkyl group, a cycloalkyl group, an aryl group, or an aralkyl group, provided that some or all of the hydrogen atoms included in $R^A$ may be substituted with a substituent, and $R^B$ represents an alkyl group or an aralkyl group, provided that some or all of the hydrogen atoms included in $R^B$ may be substituted with a substituent.

When the photoresist composition further includes at least one compound (C) selected from the group consisting of the compound shown by the formula (3-1) and the compound shown by the formula (3-2), it is possible to appropriately control diffusion of an acid generated by the acid generator (B) upon exposure, and the photoresist composition exhibits further improved lithographic performance (e.g., MEEF and LWR). The photoresist composition also exhibits sufficient basic properties (e.g., sensitivity).

A resist pattern-forming method according to one embodiment of the invention includes (1) applying the photoresist composition to a substrate to form a resist film, (2) exposing the resist film by applying radiation to the resist film via a photomask, (3) heating the exposed resist film, and (4) developing the heated resist film.

A fine resist pattern that exhibits excellent lithographic performance (e.g., MEEF and LWR) can be formed by utilizing the resist pattern-forming method.

A polymer according to one embodiment of the invention includes a structural unit shown by the following formula (1).

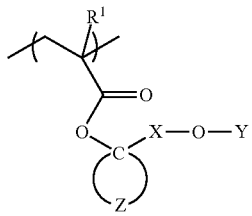

(1)

wherein $R^1$ represents a hydrogen atom, a fluorine atom, a methyl group, or a trifluoromethyl group, Z represents a group that forms a divalent alicyclic group having 3 to 20 carbon atoms together with the carbon atom bonded to X, X represents an alkanediyl group having 1 to 6 carbon atoms, Y represents a hydrogen atom or $-CR^2R^3(OR^4)$, and $R^2$ to $R^4$ independently represent a hydrogen atom or a monovalent hydrocarbon group, provided that $R^3$ and $R^4$ may bond to each other to form a cyclic ether structure together with the carbon atom bonded to $R^3$ and the oxygen atom bonded to $R^4$.

A photoresist composition that includes the polymer that includes the structural unit (I) having the above specific structure exhibits sufficient basic properties (e.g., sensitivity), and exhibits excellent lithographic performance (e.g., MEEF and LWR). The polymer may suitably be used as a material for a photoresist composition.

A compound according to one embodiment of the invention is shown by the following formula (i).

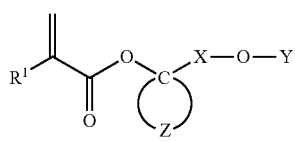

(i)

wherein $R^1$ represents a hydrogen atom, a fluorine atom, a methyl group, or a trifluoromethyl group, Z represents a group that forms a divalent alicyclic group having 3 to 20 carbon atoms together with the carbon atom bonded to X, X represents an alkanediyl group having 1 to 6 carbon atoms, Y represents a hydrogen atom or $-CR^2R^3(OR^4)$, and $R^2$ to $R^4$ independently represent a hydrogen atom or a monovalent hydrocarbon group, provided that $R^3$ and $R^4$ may bond to each other to form a cyclic ether structure together with the carbon atom bonded to $R^3$ and the oxygen atom bonded to $R^4$.

Since the compound has the structure shown by the formula (i), the compound may suitably be used as a monomer compound for incorporating the structural unit (I) in a polymer.

Note that the term "radiation" used herein includes visible rays, ultraviolet rays, deep ultraviolet rays, X-rays, charged particle rays, EUV light, and the like.

Since the photoresist composition according to one embodiment of the invention exhibits sufficient basic properties (e.g., sensitivity), and exhibits excellent lithographic performance (e.g., MEEF and LWR), the photoresist composition may be used for a lithographic process.

The embodiments of the invention are described below. Note that the invention is not limited to the following embodiments.

Photoresist Composition

The photoresist composition according to one embodiment of the invention includes the polymer (A) and the acid generator (B). The photoresist composition may include the compound (C) as a preferable component, and may further include an additional optional component as long as the effects of the invention are not impaired. Each component is described in detail below.

Polymer (A)

The polymer (A) includes the structural unit (I) shown by the formula (1). The photoresist composition that includes the polymer (A) exhibits sufficient basic properties (e.g., sensitivity), and exhibits improved lithographic performance (e.g., MEEF and LWR). It is conjectured that the above effects are obtained for the following reason, for example. Specifically, since the structural unit (I) has a structure in which a hydroxyl group or an acetal group is positioned in a specific area near the main chain of the polymer, the motion of the molecular chain of the polymer is suppressed due to interaction between the structural units (I) in the polymer. Therefore, diffusion of an acid generated by the acid generator (B) in the exposure step is appropriately suppressed. As a result, the photoresist composition achieves the above effects.

The polymer (A) preferably includes the structural unit (II) in addition to the structural unit (I). The polymer (A) may include an additional structural unit other than the structural unit (I) and the structural unit (II) as long as the effects of the invention are not impaired. Examples of the additional structural unit include a structural unit (III) that includes a lactone structure, a sultone structure, or a cyclic carbonate structure, a structural unit (IV) that includes a polar group (excluding the structural unit (I)), and the like. Each structural unit is described in detail below.

Structural Unit (I)

The structural unit (I) is shown by the formula (1).

$R^1$ in the formula (1) represents a hydrogen atom, a fluorine atom, a methyl group, or a trifluoromethyl group, Z represents a group that forms a divalent alicyclic group having 3 to 20 carbon atoms together with the carbon atom bonded to X, X represents an alkanediyl group having 1 to 6 carbon atoms, Y represents a hydrogen atom or $-CR^2R^3(OR^4)$, and $R^2$ to $R^4$ independently represent a hydrogen atom or a monovalent hydrocarbon group, provided that $R^3$ and $R^4$ may bond to each other to form a cyclic ether structure together with the carbon atom bonded to $R^3$ and the oxygen atom bonded to $R^4$.

Examples of the divalent alicyclic group having 3 to 20 carbon atoms formed by Z together with the carbon atom bonded to X include monoalicyclic groups such as a cyclopropanediyl group, a cyclobutanediyl group, a cyclopentanediyl group, a cyclohexanediyl group, a cycloheptanediyl group, a cyclooctanediyl group, a cyclodecanediyl group, a cyclododecanediyl group, a cyclobutenediyl group, a cyclopentenediyl group, a cyclohexenediyl group, a cyclodecenediyl group, a cyclododecenediyl group, a cyclopentadienediyl group, a cyclohexadienediyl group, and a cyclodecadienediyl group; and polyalicyclic groups such as a bicyclo[2.2.1]heptenediyl group, a bicyclo[2.2.2]octanediyl group, a tricyclo[5.2.1.0$^{2,6}$]decanediyl group, a tricyclo[3.3.1.1$^{3,7}$]decanediyl group, a tetracyclo[6.2.1.1$^{3,6}$.0$^{2,7}$]dodecanediyl group, an adamantanediyl group, a bicyclo[2.2.1]heptenediyl group, a bicyclo[2.2.2]octenediyl group, a tricyclo[5.2.1.0$^{2,6}$]decenediyl group, a tricyclo[3.3.1.1$^{3,7}$]decenediyl group, and a tetracyclo[6.2.1.1$^{3,6}$.0$^{2,7}$]dodecenediyl group.

A monoalicyclic group having 5 to 8 carbon atoms is preferable as the monoalicyclic group, and an adamantanediyl group is preferable as the polyalicyclic group from the viewpoint of improving the lithographic performance (e.g., MEEF and LWR). A monoalicyclic group having 5 to 8 carbon atoms is particularly preferable as the divalent alicyclic group having 3 to 20 carbon atoms.

Examples of the alkanediyl group having 1 to 6 carbon atoms represented by X include a methylene group, an ethylene group, a propanediyl group, a butanediyl group, and the like. X preferably represents an alkanediyl group having 2 to 4 carbon atoms since it is preferable that a hydroxyl group or an acetal group represented by Y in the structural unit (I) is positioned at a moderate distance from the main chain of the polymer.

It is preferable that Y represent $-CR^2R^3(OR^4)$. When Y represents such an acetal group, cleavage of the acetal occurs in the exposed area to produce a hydroxyl group, while cleavage of the acetal does not occur in the unexposed area due to the protecting group. Therefore, the contrast between the exposed area and the unexposed area increases, so that an excellent pattern shape is obtained. Examples of the monovalent hydrocarbon group represented by $R^2$ to $R^4$ include chain-like hydrocarbon groups having 1 to 20 carbon atoms, alicyclic groups having 3 to 20 carbon atoms, aryl groups having 6 to 20 carbon atoms, and the like.

Examples of the chain-like hydrocarbon groups having 1 to 20 carbon atoms include a methyl group, an ethyl group, a propyl group, a butyl group, a pentyl group, a hexyl group, an octyl group, a dodecyl group, and the like.

Examples of the alicyclic groups having 3 to 20 carbon atoms include a cyclopropyl group, a cyclobutyl group, a cyclopentyl group, a cyclohexyl group, a cyclooctyl group, a cyclododecyl group, and the like.

Examples of the aryl groups having 6 to 20 carbon atoms include a phenyl group, a tolyl group, a naphthyl group, and the like.

Examples of the structural unit (I) include structural units shown by the following formulas (1-1) to (1-10), and the like.

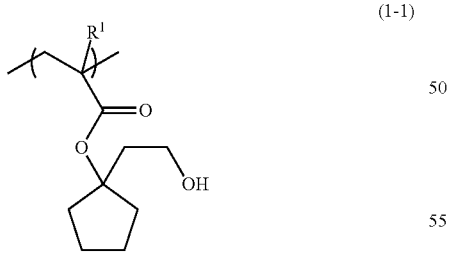

(1-1)

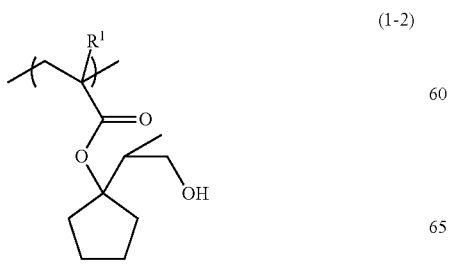

(1-2)

-continued

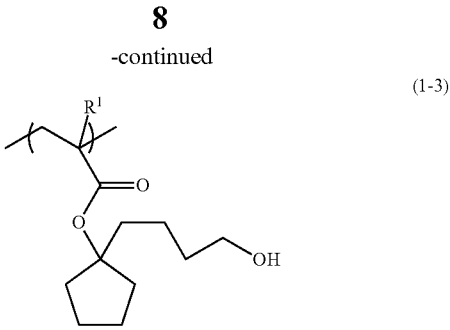

(1-3)

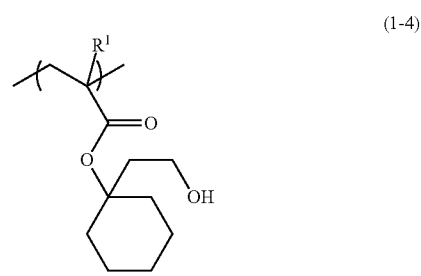

(1-4)

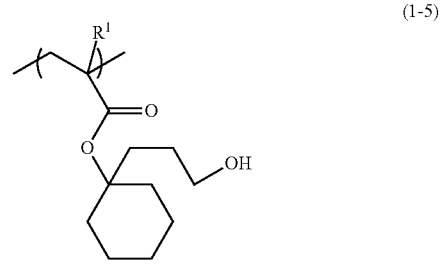

(1-5)

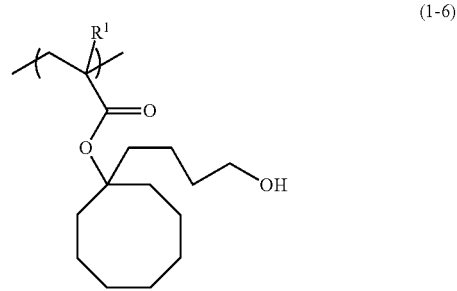

(1-6)

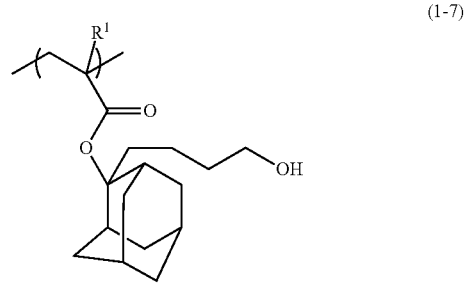

(1-7)

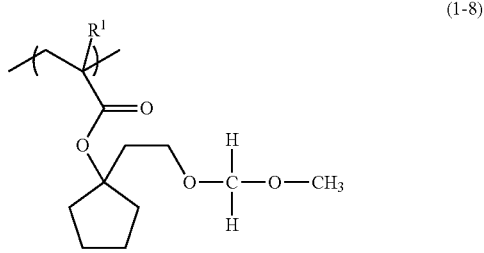

(1-8)

-continued (1-9)
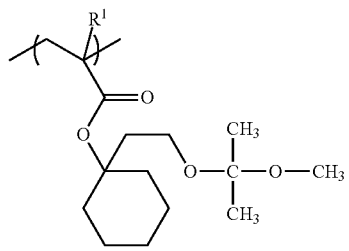

(1-10)
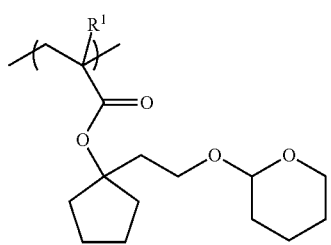

wherein R¹ is the same as defined for the formula (1).

Among these, the structural units shown by the formulas (1-1) to (1-3) and (1-6) to (1-9) are preferable since the lithographic performance (e.g., MEEF and LWR) of the photoresist composition is improved.

The content of the structural unit (I) in the polymer (A) is preferably 5 to 90 mol %, more preferably 10 to 70 mol %, and still more preferably 30 to 60 mol %, based on the total structural units included in the polymer (A). If the content of the structural unit (I) is within the above range, the lithographic performance (e.g., MEEF and LWR) of the photoresist composition can be improved. The polymer (A) may include only one type of the structural unit (I), or may include two or more types of the structural unit (I).

Examples of a monomer that produces the structural unit (I) include compounds shown by the following formulas (i-1) to (i-10), and the like.

(i-1)
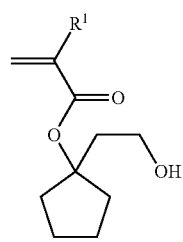

(i-2)
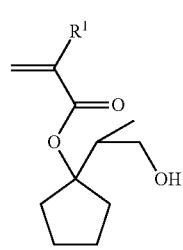

-continued (i-3)
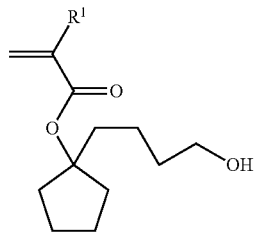

(i-4)
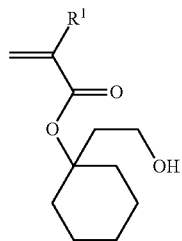

(i-5)
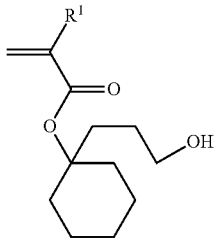

(i-6)
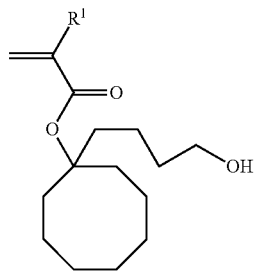

(i-7)
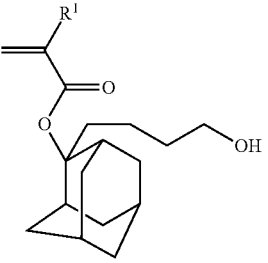

(i-8)
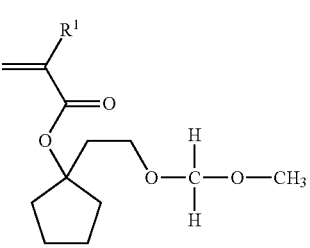

-continued

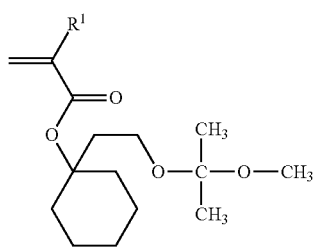
(i-9)

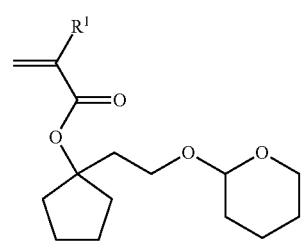
(i-10)

wherein $R^1$ is the same as defined for the formula (1).

A monomer compound that produces the structural unit (I) may be synthesized in accordance with the following scheme, for example.

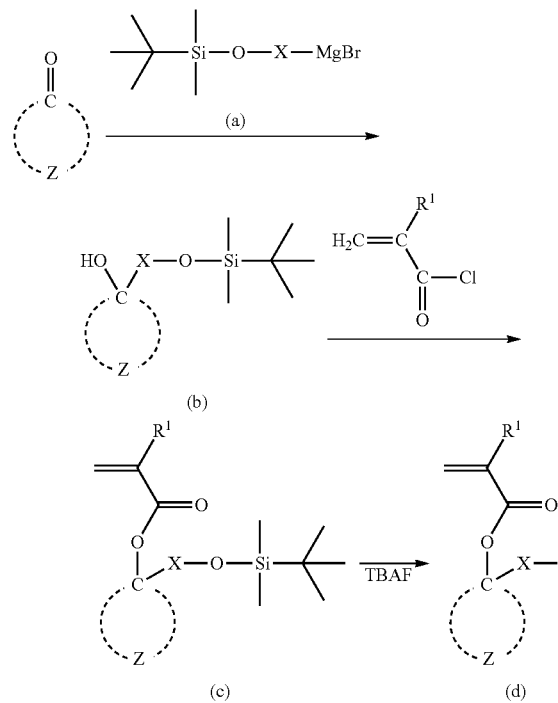

wherein $R^1$ and X are the same as defined for the formula (1).

A bromine compound (a: Grignard reagent) prepared from a linear 1-bromoalkane protected with a silyl ether and magnesium is reacted with a cyclic carbonyl compound in a solvent (e.g., diethyl ether) to obtain a compound (b). The compound (b) is reacted with (meth)acryloyl chloride or the like in the presence of a base (e.g., organic amine) to obtain a compound (c). The compound (c) is deprotected using tetrabutylammonium fluoride (TBAF) or the like to obtain a monomer compound (d) that produces the structural unit (I). The hydroxyl group of the compound (d) may optionally be acetalized.

Structural Unit (II)

The structural unit (II) is shown by the formula (2). When the polymer (A) further includes the structural unit (II) that includes an acid-labile group and has the above specific structure, the photoresist composition exhibits sufficient basic properties (e.g., sensitivity), and exhibits excellent lithographic performance (e.g., MEEF and LWR).

$R^5$ in the formula (2) represents a hydrogen atom, a fluorine atom, a methyl group, or a trifluoromethyl group, $R^{p1}$ represents a chain-like hydrocarbon group having 1 to 10 carbon atoms or an alicyclic group having 3 to 20 carbon atoms, and $R^{p2}$ and $R^{p3}$ independently represent a chain-like hydrocarbon group having 1 to 10 carbon atoms or an alicyclic group having 4 to 20 carbon atoms, provided that $R^{p2}$ and $R^{p3}$ may bond to each other to form a divalent alicyclic group having 4 to 20 carbon atoms together with the carbon atom bonded to $R^{p2}$ and $R^{p3}$.

Examples of the chain-like hydrocarbon group having 1 to 10 carbon atoms include a methyl group, an ethyl group, an n-propyl group, an i-propyl group, an n-butyl group, a 2-methylpropyl group, a 1-methylpropyl group, a t-butyl group, and the like.

Examples of the alicyclic group having 3 to 20 carbon atoms and the alicyclic group having 4 to 20 carbon atoms formed by $R^{p2}$ and $R^{p3}$ together with the carbon atom bonded to $R^{p2}$ and $R^{p3}$ include polyalicyclic groups that include a bridged skeleton (e.g., adamantane skeleton or norbornane skeleton), and monoalicyclic groups that include a cycloalkane skeleton (e.g., cyclopentane or cyclohexane). These groups may be substituted with at least one linear, branched, or cyclic alkyl group having 1 to 10 carbon atoms, for example.

The structural unit (II) is preferably any of structural units shown by the following formulas.

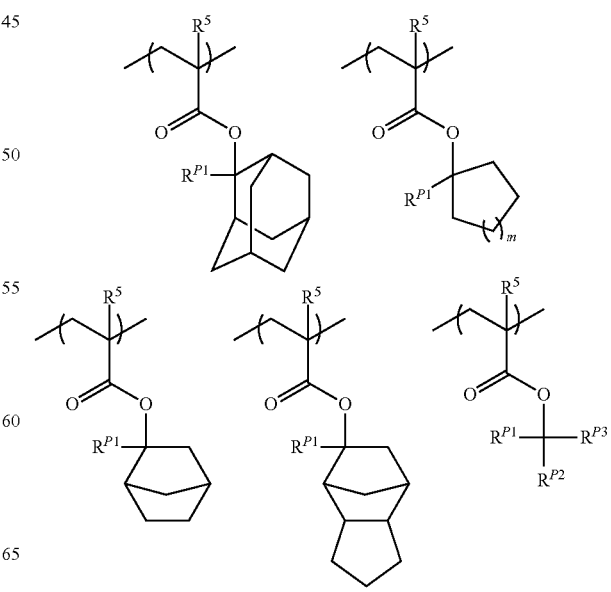

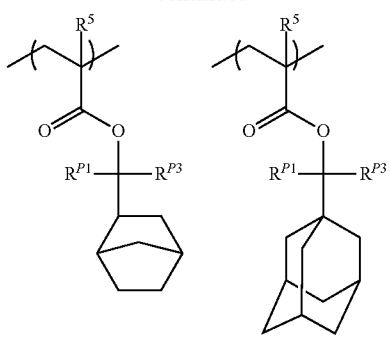
wherein $R^5$ and $R^{P1}$ to $R^{P3}$ are the same as defined for the formula (2), and m is an integer from 1 to 6.
Among these, structural units shown by the following formulas (2-1) to (2-18) are more preferable, and the structural units shown by the formulas (2-11) and (2-12) are still more preferable.
(2-1)
(2-2)
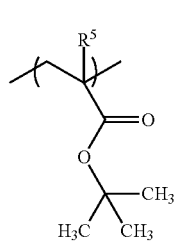
(2-3)
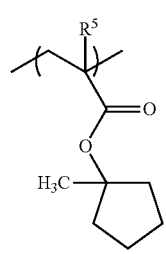
(2-4)
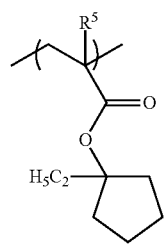
(2-5)
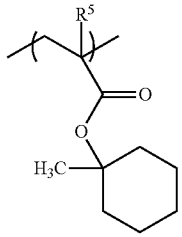
(2-6)
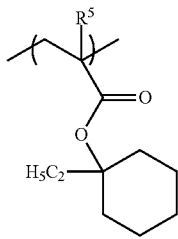
(2-7)
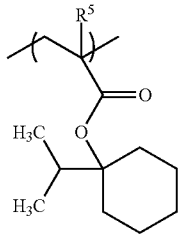
(2-8)
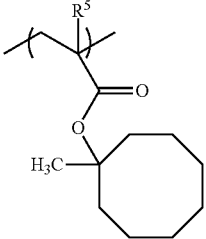
(2-9)
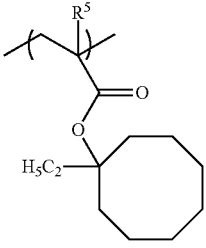
(2-10)
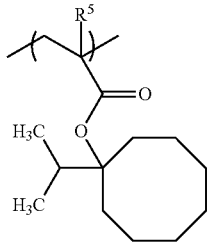

(2-11) 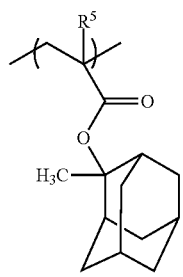

(2-12) 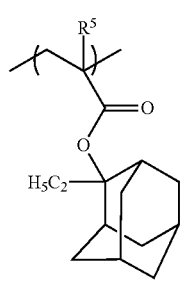

(2-13) 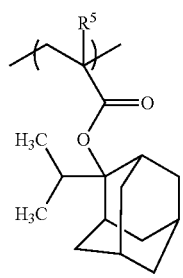

(2-14) 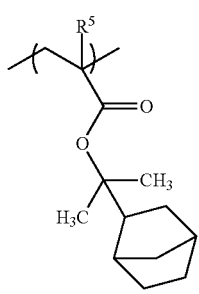

(2-15) 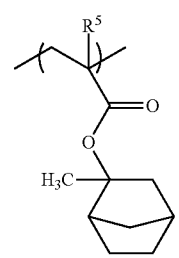

(2-16) 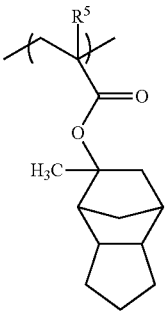

(2-17) 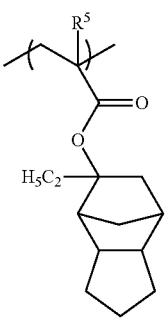

(2-18) 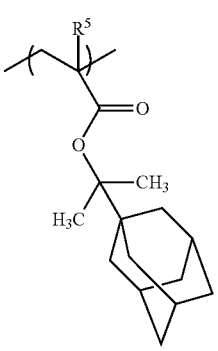

wherein $R^5$ is the same as defined for the formula (2).

The content of the structural unit (II) in the polymer (A) is preferably 5 to 80 mol %, more preferably 5 to 50 mol %, and still more preferably 5 to 20 mol %, based on the total structural units included in the polymer (A). If the content of the structural unit (II) exceeds 80 mol %, the lithographic performance (e.g., MEEF and LWR) of the photoresist composition may deteriorate. If the content of the structural unit (II) is less than 5 mol %, an excellent pattern may not be obtained due to insufficient alkali-solubility of the exposed area.

The polymer (A) may include only one type of the structural unit (II), or may include two or more types of the structural unit (II).

Examples of a monomer that produces the structural unit (II) include bicyclo[2.2.1]hept-2-yl(meth)acrylate, bicyclo[2.2.2]oct-2-yl(meth)acrylate, tricyclo[5.2.1.0$^{2,6}$]dec-7-yl(meth)acrylate, tricyclo[3.3.1.1$^{3,7}$]dec-1-yl(meth)acrylate, tricyclo[3.3.1.1$^{3,7}$]dec-2-yl(meth)acrylate, and the like.

Structural Unit (III)

The polymer (A) may further include the structural unit (III) that includes a lactone structure, a sultone structure, or a cyclic carbonate structure. When the polymer (A) includes the structural unit (III), the resulting resist film exhibits improved adhesion to the substrate.

Examples of the structural unit (III) include structural units shown by the following formulas.

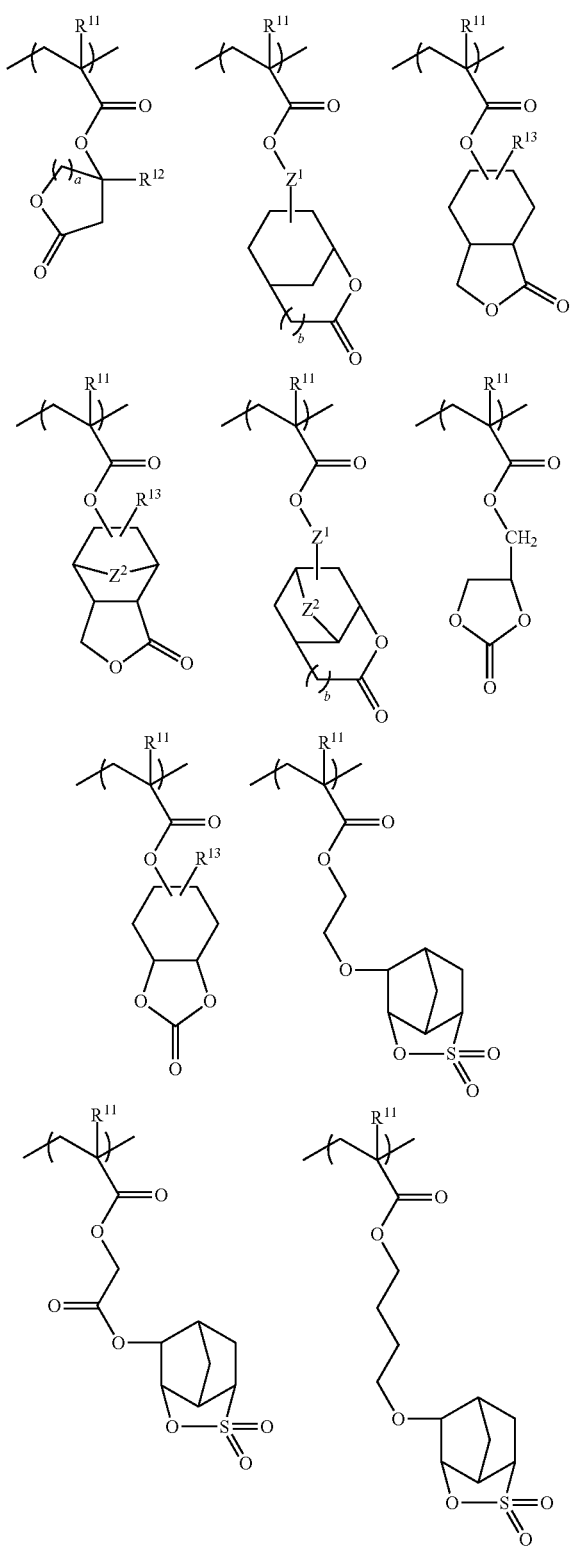

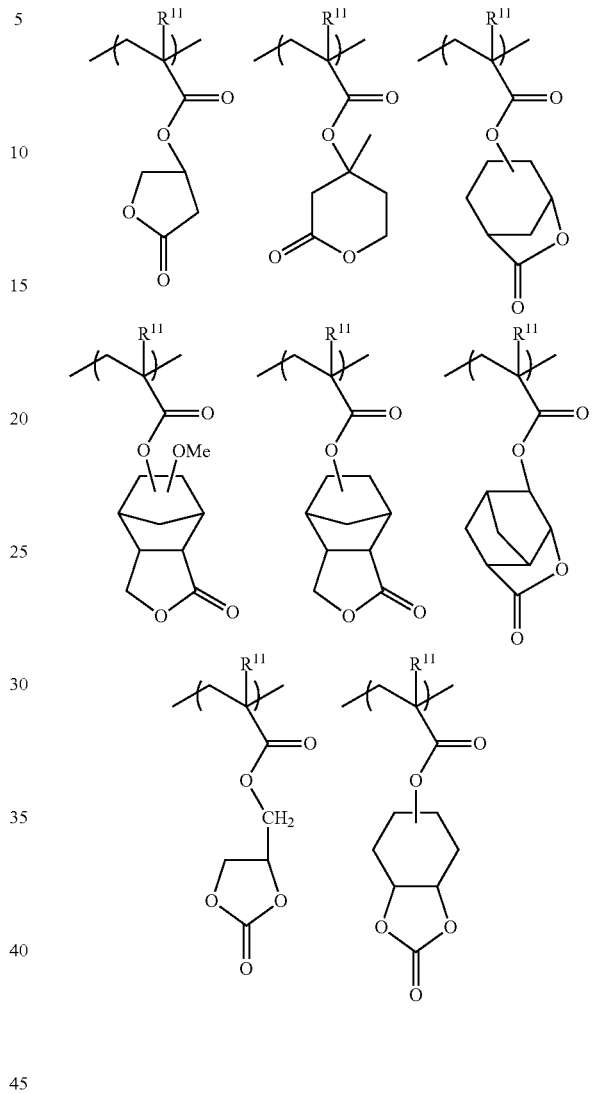

The structural unit (III) is preferably any of structural units shown by the following formulas.

wherein $R^{11}$ represents a hydrogen atom or a methyl group.

The content of the structural unit (III) in the polymer (A) is preferably 0 to 80 mol %, and more preferably 10 to 60 mol %, based on the total structural units included in the polymer (A). If the content of the structural unit (III) is within the above range, the resulting resist film exhibits improved adhesion to the substrate. If the content of the structural unit (III) exceeds 80 mol %, the lithographic performance (e.g., MEEF and LWR) of the photoresist composition may deteriorate.

Examples of a preferable monomer that produces the structural unit (III) include the monomers disclosed in WO2007/116664.

Structural Unit (IV)

The polymer (A) preferably further includes the structural unit (IV) that includes a polar group (see the following formulas) (excluding the structural unit (I)). Examples of the polar group include a hydroxyl group, a carboxyl group, a keto group, a sulfonamide group, an amino group, an amide group, and a cyano group.

wherein $R^{11}$ represents a hydrogen atom, a fluorine atom, a methyl group, or a trifluoromethyl group, $R^{12}$ represents a hydrogen atom or a methyl group, $R^{13}$ represents a hydrogen atom or a methoxy group, $Z^1$ represents a single bond or a methylene group, $Z^2$ represents a methylene group or an oxygen atom, and a and b are 0 or 1.

Examples of the structural unit (IV) include structural units shown by the following formulas.
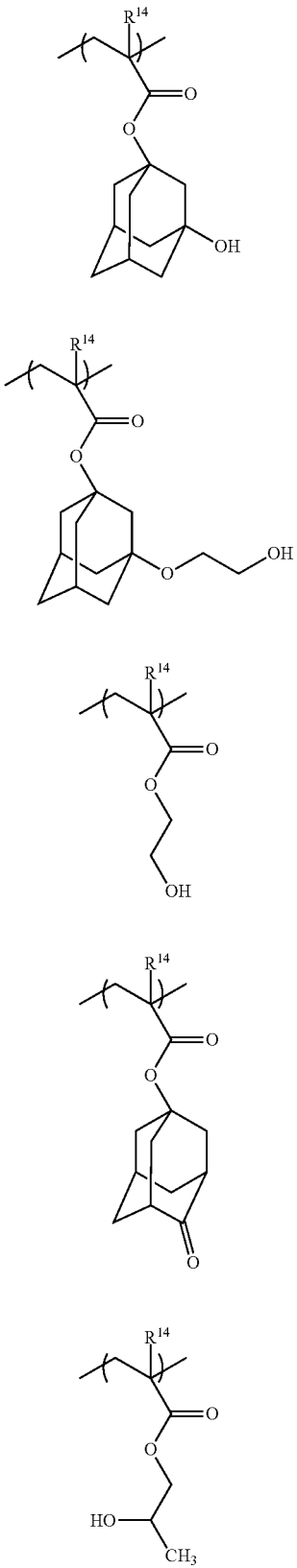
(4-1) (4-2) (4-3) (4-4) (4-5)
-continued
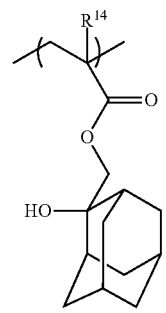
(4-6)
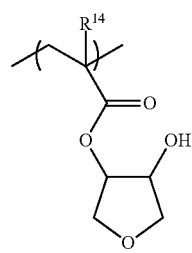
(4-7)
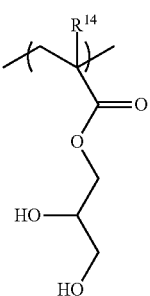
(4-8)
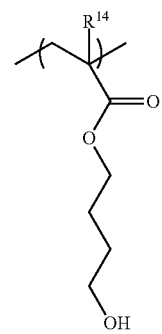
(4-9)
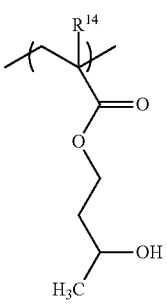
(4-10)

(4-11)

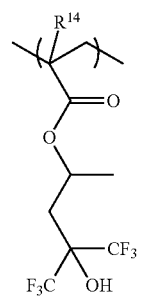

(4-12)

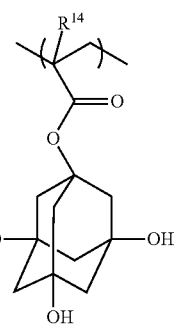

(4-13)

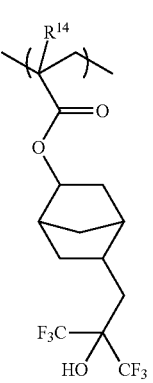

(4-14)

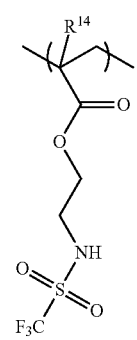

(4-15)

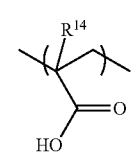

wherein $R^{14}$ represents a hydrogen atom, a fluorine atom, a methyl group, or a trifluoromethyl group.

The content of the structural unit (IV) in the polymer (A) is preferably 5 to 80 mol %, and more preferably 8 to 40 mol %, based on the total structural units included in the polymer (A).

The polymer (A) may include only one type of the structural unit (IV), or may include two or more types of the structural unit (IV).

Synthesis of Polymer (A)

The polymer (A) may be synthesized by radical polymerization or the like.

The polymer (A) is preferably synthesized by polymerizing a monomer by adding a solution containing a monomer and a radical initiator dropwise to a reaction solvent or a solution containing a monomer, polymerizing a monomer by adding a solution containing a monomer and a solution containing a radical initiator dropwise to a reaction solvent or a solution containing a monomer, or polymerizing a plurality of types of monomers by adding a plurality of solutions containing a different monomer and a solution containing a radical initiator dropwise to a reaction solvent or a solution containing a monomer, for example. When adding a monomer solution dropwise to another monomer solution, the amount of monomer in the monomer solution that is added dropwise to the other monomer solution is preferably 30 mol % or more, more preferably 50 mol % or more, and particularly preferably 70 mol % or more, based on the total amount of monomer subjected to polymerization. The above monomer (i.e., the compound according to one embodiment of the invention shown by the formula (i)) is synthesized by a method described later.

The reaction temperature may be appropriately determined depending on the type of initiator. The reaction temperature is normally 30 to 180° C., preferably 40 to 160° C., and more preferably 50 to 140° C. The dropwise addition time is determined depending on the reaction temperature, the type of initiator, the type of monomer, and the like, but is normally 30 minutes to 8 hours, preferably 45 minutes to 6 hours, and more preferably 1 to 5 hours. The total reaction time including the dropwise addition time is also determined depending on the reaction conditions, but is normally 30 minutes to 8 hours, preferably 45 minutes to 7 hours, and more preferably 1 to 6 hours.

Examples of the radical initiator used for polymerization include azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile), and the like. These initiators may be used either alone or in combination.

The polymerization solvent is not particularly limited as long as the polymerization solvent does not hinder polymerization (e.g., nitrobenzene has a polymerization inhibiting effect, and a mercapto compound has a chain transfer effect) and can dissolve the monomer. Examples of the polymerization solvent include alkanes such as n-pentane, n-hexane, n-heptane, n-octane, n-nonane, and n-decane; cycloalkanes such as cyclohexane, cycloheptane, cyclooctane, decalin, and norbornane; aromatic hydrocarbons such as benzene, toluene, xylene, ethylbenzene, and cumene; halogenated hydrocarbons such as chlorobutanes, bromohexanes, dichloroethanes, hexamethylene dibromide, and chlorobenzene; saturated carboxylates such as ethyl acetate, n-butyl acetate, i-butyl acetate, and methyl propionate; ketones such as acetone, 2-butanone, 4-methyl-2-pentanone, and 2-heptanone; ethers such as tetrahydrofuran, dimethoxyethanes, and diethoxyethanes; alcohols such as methanol, ethanol, 1-propanol, 2-propanol, and 4-methyl-2-pentanol; and the like. These solvents may be used either alone or in combination.

The resin obtained by polymerization is preferably collected by re-precipitation. Specifically, the polymer solution is poured into a re-precipitation solvent after completion of polymerization to collect the target resin as a powder. An alcohol, an alkane, or the like may be used as the re-precipitation solvent either alone or in combination. The resin may also be collected by removing low-molecular-weight components (e.g., monomer and oligomer) by performing a separation operation, a column operation, an ultrafiltration operation, or the like.

The polystyrene-reduced weight average molecular weight (Mw) of the polymer (A) determined by gel permeation chromatography (GPC) is not particularly limited, but is preferably 1000 to 100,000, more preferably 2000 to 50,000, and particularly preferably 3000 to 20,000. If the Mw of the polymer (A) is within the above range, the photoresist composition exhibits excellent sensitivity, excellent lithographic performance (e.g., LWR and DOF), and excellent etching resistance.

The ratio (Mw/Mn) of the Mw to the polystyrene-reduced number average molecular weight (Mn) of the polymer (A) determined by GPC is normally 1 to 5, preferably 1 to 3, and more preferably 1 to 2. If the ratio (Mw/Mn) of the Mw to the Mn of the polymer (A) is within the above range, the photoresist composition exhibits excellent sensitivity, excellent lithographic performance (e.g., LWR and DOF), and excellent etching resistance.

Note that the terms "Mw" and "Mn" used herein refer to values determined by GPC using GPC columns (manufactured by Tosoh Corporation, G2000HXL×2, G3000HXL×1, G4000HXL×1) at a flow rate of 1.0 ml/min and a column temperature of 40° C. (eluant: tetrahydrofuran, standard: monodisperse polystyrene).

Acid Generator (B)

The acid generator (B) generates an acid upon exposure, and the acid-labile group included in the polymer (A) dissociates due to the acid generated by the acid generator (B) to generate an acid. As a result, the polymer (A) becomes soluble in a developer.

The acid generator (B) may be included in the photoresist composition as a compound (described below) and/or may be included in the polymer.

Examples of the acid generator (B) include onium salt compounds, sulfonimide compounds, halogen-containing compounds, diazoketone compounds, and the like. Among these, it is preferable to use an onium salt compound as the acid generator (B).

Examples of the onium salt compounds include sulfonium salts (including tetrahydrothiophenium salts), iodonium salts, phosphonium salts, diazonium salts, pyridinium salts, and the like.

Examples of the sulfonium salts include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, triphenylphosphonium 1,1,2,2-tetrafluoro-6-(1-adamantanecarbonyloxy)-hexane-1-sulfonate, and the like. Among these, triphenylsulfonium trifluoromethanesulfonate, triphenylsulfonium nonafluoro-n-butanesulfonate, and triphenylphosphonium 1,1,2,2-tetrafluoro-6-(1-adamantanecarbonyloxy)-hexane-1-sulfonate are preferable.

Examples of the tetrahydrothiophenium salts include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, and the like. Among these, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, and 1-(3,5-dimethyl-4-hydroxyphenyl)tetrahydrothiophenium nonafluoro-n-butanesulfonate are preferable.

Examples of the iodonium salts include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and the like. Among these, bis(4-t-butylphenyl)iodonium nonafluoro-n-butanesulfonate is preferable.

Examples of sulfonyloxyimide compounds include N-(trifluoromethanesulfonyloxy)bicyclo[2.2.1]hept-5-ene-2,3-dicarboxylmide, N-(nonafluoro-n-butanesulfonyloxy)bicyclo[2.2.1]hept-5-ene-2,3-dicarboxylmide, N-(perfluoro-n-octanesulfonyloxy)bicyclo[2.2.1]hept-5-ene-2,3-dicarboxylmide, N-(2-bicyclo[2.2.1]hept-2-yl-1,1,2,2-tetrafluoroethanesulfonyloxy)bicyclo[2.2.1]hept-5-ene-2,3-dicarboxylmide, and the like. Among these, N-(trifluoromethanesulfonyloxy)bicyclo[2.2.1]hept-5-ene-2,3-dicarboxylmide is preferable.

These acid generators (B) may be used either alone or in combination. The acid generator (B) is normally used in an amount of 0.1 to 20 parts by mass, and preferably 0.5 to 15 parts by mass, based on 100 parts by mass of the polymer (A), in order to ensure that the resulting resist exhibits sufficient sensitivity and developability. If the amount of the acid generator (B) is less than 0.1 parts by mass, the resulting resist may exhibit insufficient sensitivity and developability. If the amount of the acid generator (B) exceeds 15 parts by mass, the desired resist pattern may not be obtained due to a decrease in radiation transmittance.

Compound (C)

The compound (C) functions as an acid diffusion controller that controls a phenomenon in which an acid generated by the acid generator (B) upon exposure is diffused in the resist film, and suppresses undesired chemical reactions in the unexposed area. The compound (C) is decomposed upon exposure, and loses acid diffusion controllability. Therefore, the compound (C) allows diffusion of an acid in the exposed area, but controls diffusion of an acid in the unexposed area, so that the contrast between the exposed area and the unexposed area is improved (i.e., the boundary between the exposed area and the unexposed area becomes distinct). This is effective for improving the LWR and the MEEF of the photoresist composition according to one embodiment of the invention. Moreover, the photoresist composition that includes the compound (C) exhibits improved storage stability and improved resolution, and suppresses a change in line width of the resist pattern due to a change in post-exposure delay from exposure to development. The photoresist composition that includes the compound (C) also exhibits excellent process stability. The compound (C) may be included in the photoresist composition as a free compound, and/or may be included in the polymer.

The compound (C) is at least one compound selected from the group consisting of the compound shown by the formula (3-1) and the compound shown by the formula (3-2).

$R^6$ to $R^{10}$ in the formulas (3-1) and (3-2) independently represent a hydrogen atom, an alkyl group, an alkoxy group, a hydroxyl group, or a halogen atom, $E^-$ and $G^-$ independently represent $OH^-$, $R^A$—$COO^-$, $R^A$—$SO_3^-$, or $R^A$—$N^-$—$SO_2$—$R^B$, $R^A$ represents an alkyl group, a cycloalkyl group, an aryl group, or an aralkyl group, provided that some or all of the hydrogen atoms included in $R^A$ may be substituted with a substituent, and $R^B$ represents an alkyl group or an aralkyl group, provided that some or all of the hydrogen atoms included in $R^B$ may be substituted with a substituent.

Examples of the alkyl group represented by $R^6$ to $R^{10}$ in the formulas (3-1) and (3-2) include a methyl group, an ethyl group, a propyl group, a butyl group, and the like.

Examples of the alkoxy group represented by $R^6$ to $R^{10}$ include a methoxy group, an ethoxy group, a propoxy group, a butoxy group, and the like.

Examples of the halogen atom represented by $R^6$ to $R^{10}$ include a fluorine atom, a chlorine atom, a bromine atom, an iodine atom, and the like.

Examples of the alkyl group represented by $R^A$ and $R^B$ include a methyl group, an ethyl group, a propyl group, a butyl group, and the like.

Examples of the cycloalkyl group represented by $R^A$ include a cyclopentyl group, a cyclohexyl group, a norbornyl group, and the like.

Examples of the aryl group represented by $R^A$ include a phenyl group, a naphthyl group, and the like.

Examples of the aralkyl group represented by $R^A$ and $R^B$ include a benzyl group, a phenethyl group, a naphthylmethyl group, a naphthylethyl group, a naphthylbutyl group, and the like.

A substituent that may substitute $R^A$ is preferably a hydroxyl group or a cyano group. Examples of the group represented by $R^A$ that is substituted with a substituent include hydroxyalkyl groups having 1 to 4 carbon atoms (e.g., hydroxymethyl group), cyanoalkyl groups having 2 to 5 carbon atoms (e.g., cyanomethyl group), monovalent groups derived from an alicyclic group (e.g., cycloalkane skeleton (e.g., hydroxycyclopentane, hydroxycyclohexane, or cyclohexanone) or bridged hydrocarbon skeleton (e.g., 1,7,7-trimethylbicyclo[2.2.1]heptan-2-one (camphor)), groups obtained by substituting an aryl group with a hydroxyl group or a cyano group, and the like. Among these, a hydroxymethyl group, a cyanomethyl group, a group derived from 1,7,7-trimethylbicyclo[2.2.1]heptan-2-one, and a group obtained by substituting a phenyl group, a benzyl group, or a phenylcyclohexyl group with a hydroxyl group or a cyano group are preferable.

When $E^-$ and $G^-$ represent a sulfonate anion ($R^A$—$SO_3^-$), a carbon atom bonded to a fluorine atom or a perfluoroalkyl group is not bonded directly to the sulfonate group.

$E^-$ in the formula (3-1) preferably represents the anion shown by the following formula (3-1-1) (i.e., an anion shown by $R^A$—$COO^-$ wherein $R^A$ represents a phenyl group), the anion shown by the following formula (3-1-2) (i.e., an anion shown by $R^A$—$SO_3^-$ wherein $R^A$ represents a group derived from 1,7,7-trimethylbicyclo[2.2.1]heptan-2-one), or the anion shown by the following formula (3-1-3) (i.e., an anion shown by $R^A$—$N^-$—$SO_2$—$R^B$ wherein $R^A$ represents a butyl group, and $R^B$ represents a trifluoromethyl group).

(3-1-1)

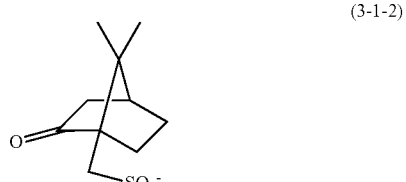

(3-1-2)

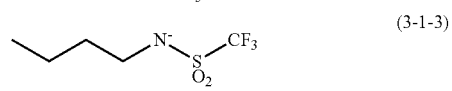

(3-1-3)

The compound (C) (i.e., at least one compound selected from the group consisting of the compound shown by the formula (3-1) and the compound shown by the formula (3-2)) is a sulfonium salt compound or an iodonium salt compound that satisfies the above conditions.

Examples of the sulfonium salt compound include triphenylsulfonium hydroxide, triphenylsulfonium salicylate, triphenylsulfonium 4-trifluoromethyl salicylate, diphenyl-4-hydroxyphenylsulfonium salicylate, triphenylsulfonium 10-camphorsulfonate, 4-t-butoxyphenyl.diphenylsulfonium 10-camphorsulfonate, and the like.

These sulfonium salt compounds may be used either alone or in combination.

Examples of the iodonium salt compound include bis(4-t-butylphenyl)iodonium hydroxide, bis(4-t-butylphenyl)iodonium salicylate, bis(4-t-butylphenyl)iodonium 4-trifluoromethyl salicylate, bis(4-t-butylphenyl)iodonium 10-camphorsulfonate, and the like. These iodonium salt compounds may be used either alone or in combination.

These compounds (C) may be used either alone or in combination. The compound (C) is preferably used in an amount of less than 10 parts by mass based on 100 parts by mass of the polymer (A). If the amount of the compound (C) exceeds 10 parts by mass, the sensitivity of the resulting resist may decrease.

Additional Optional Component

The photoresist composition may include an additive (e.g., solvent, fluorine-containing polymer, surfactant, alicyclic skeleton-containing compound, or sensitizer) as an additional optional component in addition to the polymer (A), the acid generator (B), and the compound (C) (preferable component) as long as the effects of the invention are not impaired.

Fluorine-Containing Polymer

The photoresist composition may further include a fluorine-containing polymer. The term "fluorine-containing polymer" used herein refers to a polymer that includes a fluorine atom. When the photoresist composition includes the fluorine-containing polymer, elution of a substance during liquid immersion lithography can be suppressed since the hydrophobicity of the resist film is improved. Moreover, since the receding contact angle of the resist film with an immersion medium can be sufficiently increased, water droplets do not remain when performing a high-speed scan, for example. Therefore, the photoresist composition may suitably be used for liquid immersion lithography.

The fluorine-containing polymer is produced by polymerizing at least one monomer that includes a fluorine atom in its structure.

Examples of the monomer that produces a polymer that includes a fluorine atom in its structure include monomers that include a fluorine atom in the main chain, monomers that include a fluorine atom in the side chain, and monomers that include a fluorine atom in the main chain and the side chain.

Examples of the monomers that produce a polymer that includes a fluorine atom in the main chain include α-fluoroacrylate compounds, α-trifluoromethyl acrylate compounds, β-fluoroacrylate compounds, β-trifluoromethyl acrylate compounds, α,β-fluoroacrylate compounds, α,β-trifluoromethyl acrylate compounds, compounds in which a hydrogen atom of at least one vinyl site is substituted with a fluorine atom, a trifluoromethyl group, or the like, and the like.

Examples of the monomers that produce a polymer that includes a fluorine atom in the side chain include compounds obtained by substituting the side chain of an alicyclic olefin compound (e.g., norbornene) with a fluorine atom or a fluoroalkyl group, derivatives thereof, fluoroalkyl acrylates, fluoroalkyl methacrylates, derivatives thereof, compounds obtained by substituting the side chain (i.e., a site that does not include a double bond) of an olefin with a fluorine atom or a fluoroalkyl group, derivatives thereof, and the like.

Examples of the monomers that produce a polymer that includes a fluorine atom in the main chain and the side chain include α-fluoroacrylic acid, β-fluoroacrylic acid, α,β-fluoroacrylic acid, α-trifluoromethylacrylic acid, β-trifluoromethylacrylic acid, α,β-trifluoromethylacrylic acid, ester compounds (derivatives) thereof, compounds obtained by substituting the side chain of a compound in which a hydrogen atom of at least one vinyl site is substituted with a fluorine atom, a trifluoromethyl group, or the like, with a fluorine atom or a fluoroalkyl group, derivatives thereof, compounds obtained by substituting a hydrogen atom bonded to the double bond of an alicyclic olefin compound with a fluorine atom, a trifluoromethyl group, or the like, and substituting the side chain of the alicyclic olefin compound with a fluoroalkyl group, derivatives thereof, and the like. Note that the term "alicyclic olefin compound" used herein refers to a compound that includes a double bond in its ring structure.

Specific examples of the structural unit included in the fluorine-containing polymer include a structural unit shown by the following formula (hereinafter may be referred to as "structural unit (V)").

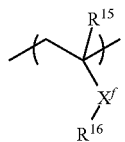

wherein $R^{15}$ represents a hydrogen atom, a methyl group, or a trifluoromethyl group, $X^f$ represents a linking group, and $R^{16}$ represents a linear or branched alkyl group having 1 to 6 carbon atoms that includes at least one fluorine atom, a monovalent alicyclic hydrocarbon group having 4 to 20 carbon atoms, or a derivative thereof.

Examples of the linking group represented by $X^f$ include a single bond, an oxygen atom, a sulfur atom, a carbonyloxy group, an oxycarbonyl group, an amide group, a sulfonylamide group, a urethane group, and the like.

Examples of a monomer that produces the structural unit (V) include 2-[1-(ethoxycarbonyl)-1,1-difluorobutyl](meth)acrylate, trifluoromethyl(meth)acrylate, 2,2,2-trifluoroethyl (meth)acrylate, perfluoroethyl(meth)acrylate, perfluoro-n-propyl (meth)acrylate, perfluoro-1-propyl(meth)acrylate, perfluoro-n-butyl(meth)acrylate, perfluoro-1-butyl(meth) acrylate, perfluoro-t-butyl(meth)acrylate, 2-(1,1,1,3,3,3-hexafluoropropyl) (meth)acrylate, 1-(2,2,3,3,4,4,5,5-octafluoropentyl) (meth)acrylate, perfluorocyclohexylmethyl (meth)acrylate, 1-(2,2,3,3,3-pentafluoropropyl) (meth) acrylate, 1-(3,3,4,4,5,5,6,6,7,7,8,8,9,9,10,10,10-heptadecafluorodecyl) (meth)acrylate, 1-(5-trifluoromethyl-3,3,4,4,5,6,6,6-octafluorohexyl) (meth)acrylate, and the like.

The fluorine-containing polymer may include only one type of the structural unit (V), or may include two or more types of the structural unit (V). The content of the structural unit (V) in the fluorine-containing polymer is normally 5 mol % or more, preferably 10 mol % or more, and more preferably 15 mol % or more, based on the total structural units (=100 mol %) included in the fluorine-containing polymer. If the content of the structural unit (V) is less than 5 mol %, a receding contact angle equal to or more than 70° may not be achieved, or elution of the acid generator and the like from the resist film may not be suppressed.

The fluorine-containing polymer may further include one or more additional structural units such as a structural unit that includes an acid-labile group and controls the dissolution rate in a developer, a structural unit that includes a lactone structure, a hydroxyl group, a carboxyl group, or the like, and a structural unit that is derived from an aromatic compound and suppresses light scattering due to reflection from the substrate.

Examples of the additional structural unit that includes an acid-labile group include the structural units mentioned above in connection with the structural unit (II) that may be included in the polymer (A). Examples of the additional structural unit that includes a lactone structure or the like include the structural units mentioned above in connection with the structural unit (III) that may be included in the polymer (A). Examples of the additional structural unit that includes a polar group include the structural units mentioned above in connection with the structural unit (IV) that may be included in the polymer (A).

Examples of a preferable monomer that produces the additional structural unit derived from an aromatic compound include styrene, α-methylstyrene, 2-methylstyrene, 3-methylstyrene, 4-methylstyrene, 2-methoxystyrene, 3-methoxystyrene, 4-methoxystyrene, 4-(2-t-butoxycarbonylethyloxy) styrene, 2-hydroxystyrene, 3-hydroxystyrene, 4-hydroxystyrene, 2-hydroxy-α-methylstyrene, 3-hydroxy-α-methylstyrene, 4-hydroxy-α-methylstyrene, 2-methyl-3-hydroxystyrene, 4-methyl-3-hydroxystyrene, 5-methyl-3-hydroxystyrene, 2-methyl-4-hydroxystyrene, 3-methyl-4-hydroxystyrene, 3,4-dihydroxystyrene, 2,4,6-trihydroxystyrene, 4-t-butoxystyrene, 4-t-butoxy-α-methylstyrene, 4-(2-ethyl-2-propoxy)styrene, 4-(2-ethyl-2-propoxy)-α-methylstyrene, 4-(1-ethoxyethoxy)styrene, 4-(1-ethoxyethoxy)-α-methylstyrene, phenyl(meth)acrylate, benzyl(meth)acrylate, acenaphthylene, 5-hydroxyacenaphthylene, 1-vinylnaphthalene, 2-vinylnaphthalene, 2-hydroxy-6-vinylnaphthalene, 1-naphthyl(meth)acrylate, 2-naphthyl(meth)acrylate, 1-naphthylmethyl(meth)acrylate, 1-anthryl(meth)acrylate, 2-anthryl(meth)acrylate, 9-anthryl(meth)acrylate, 9-anthrylmethyl(meth)acrylate, 1-vinylpyrene, and the like.

The content of the additional structural unit in the fluorine-containing polymer is normally 80 mol % or less, preferably 75 mol % or less, and more preferably 70 mol % or less, based on the total structural units included in the fluorine-containing polymer.

The Mw of the fluorine-containing polymer is preferably 1000 to 50,000, more preferably 1000 to 30,000, and particularly preferably 1000 to 10,000. If the Mw of the fluorine-containing polymer is less than 1000, a sufficient receding contact angle may not be obtained. If the Mw of the fluorine-containing polymer exceeds 50,000, the resulting resist may exhibit poor developability. The ratio (Mw/Mn) of the Mw to the Mn of the fluorine-containing polymer is normally 1 to 3, and preferably 1 to 2.

The fluorine-containing polymer is preferably used in an amount of 0 to 50 parts by mass, more preferably 0 to 20 parts by mass, particularly preferably 0.5 to 10 parts by mass, and most preferably 1 to 8 parts by mass, based on 100 parts by mass of the polymer (A). If the amount of the fluorine-containing polymer is within the above range, the water repellency and the elution resistance of the surface of the resulting resist film can be further improved.

Synthesis of Fluorine-Containing Polymer

The fluorine-containing polymer may be synthesized by polymerizing a monomer that produces each structural unit in an appropriate solvent using a radical initiator, for example.

Examples of the solvent used for polymerization include those mentioned above in connection with synthesis of the polymer (A).

The reaction (polymerization) temperature is normally 40 to 150° C., and preferably 50 to 120° C. The reaction time is normally 1 to 48 hours, and preferably 1 to 24 hours.

Solvent

The photoresist composition normally includes a solvent. The solvent is not particularly limited as long as the solvent can dissolve the polymer (A), the acid generator (B), the compound (C) (preferable component), and an optional component. Examples of the solvent include alcohol solvents, ether solvents, ketone solvents, amide solvents, ester solvents, a mixture thereof, and the like.

Examples of the alcohol solvents include monohydric alcohol solvents such as methanol, ethanol, n-propanol, isopropanol, n-butanol, isobutanol, sec-butanol, tert-butanol, n-pentanol, isopentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol, and diacetone alcohol; polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, and tripropylene glycol; polyhydric alcohol partial ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, and dipropylene glycol monopropyl ether; and the like.

Examples of the ether solvents include diethyl ether, dipropyl ether, dibutyl ether, diphenyl ether, methoxybenzene, and the like.

Examples of the ketone solvents include acetone, methyl ethyl ketone, methyl n-propyl ketone, methyl n-butyl ketone, diethyl ketone, methyl isobutyl ketone, methyl n-pentyl ketone, ethyl n-butyl ketone, methyl n-hexyl ketone, diisobutyl ketone, trimethylenonane, cyclopentanone, cyclohexanone, cycloheptanone, cyclooctanone, methylcyclohexanone, 2,4-pentanedione, acetonylacetone, acetophenone, and the like.

Examples of the amide solvents include N,N'-dimethylimidazolidinone, N-methylformamide, N,N-dimethylformamide, N,N-diethylformamide, acetamide, N-methylacetamide, N,N-dimethylacetamide, N-methylpropioneamide, N-methylpyrrolidone, and the like.

Examples of the ester solvents include diethyl carbonate, propylene carbonate, methyl acetate, ethyl acetate, γ-butyrolactone, γ-valerolactone, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxy triglycol acetate, ethyl propionate, n-butyl propionate, isoamyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Examples of hydrocarbon solvents include aliphatic hydrocarbon solvents such as n-pentane, isopentane, n-hexane, isohexane, n-heptane, isoheptane, 2,2,4-trimethylpentane, n-octane, isooctane, cyclohexane, and methylcyclohexane; aromatic hydrocarbon solvents such as benzene, toluene, xylene, mesitylene, ethylbenzene, trimethylbenzene, methylethylbenzene, n-propylbenzene, isopropylbenzene, diethylbenzene, isobutylbenzene, triethylbenzene, diisopropylbenzene, and n-amylnaphthalene; and the like.

Among these, propylene glycol monomethyl ether acetate, cyclohexanone, and γ-butyrolactone are preferable. These solvents may be used either alone or in combination.

Surfactant

The surfactant improves the applicability, striation, developability, and the like of the photoresist composition. Examples of the surfactant include nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, and polyethylene glycol distearate; commercially available products such as KP341 (manufactured by Shin-Etsu Chemical Co., Ltd.), Polyflow No. 75, Polyflow No. 95 (manufactured by Kyoeisha Chemical Co., Ltd.), EFTOP EF301, EFTOP EF303, EFTOP EF352 (manufactured by JEMCO, Inc.), Megafac F171, Megafac F173 (manufactured by DIC Corporation), Fluorad FC430, Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, Surflon SC-106 (manufactured by Asahi Glass Co., Ltd.); and the like. These surfactants may be used either alone or in combination.

Alicyclic Skeleton-Containing Compound

The alicyclic skeleton-containing compound improves the dry etching resistance, the pattern shape, adhesion to the substrate, and the like.

Examples of the alicyclic skeleton-containing compound include adamantane derivatives such as 1-adamantanecarboxylic acid, 2-adamantanone, and t-butyl 1-adamantanecarboxylate, deoxycholates such as t-butyl deoxycholate, t-butoxycarbonylmethyl deoxycholate, and 2-ethoxyethyl deoxycholate, lithocholates such as t-butyl lithocholate, t-butoxycarbonylmethyl lithocholate, and 2-ethoxyethyl lithocholate, 3-[2-hydroxy-2,2-bis(trifluoromethyl)ethyl]tetracyclo[$4.4.0.1^{2,5}.1^{7,10}$]dodecane, 2-hydroxy-9-methoxycarbonyl-5-oxo-4-oxatricyclo[$4.2.1.0^{3,7}$]nonane, and the like. These alicyclic skeleton-containing compounds may be used either alone or in combination.

Sensitizer

The sensitizer increases the amount of acid generated by the acid generator (B), and improves the apparent sensitivity of the photoresist composition.

Examples of the sensitizer include carbazoles, acetophenones, benzophenones, naphthalenes, phenols, biacetyl, eosine, rose bengal, pyrenes, anthracenes, phenothiazines, and the like. These sensitizers may be used either alone or in combination.

Preparation of Photoresist Composition

The photoresist composition may be prepared by mixing the polymer (A), the acid generator (B), the optional compound (C), and an additional optional component in an organic solvent in a given ratio, for example. The photoresist composition is used in a state in which the components are dissolved or dispersed in an appropriate organic solvent.

Resist Pattern-Forming Method

A resist pattern-forming method according to one embodiment of the invention includes (1) applying the photoresist composition according to one embodiment of the invention to a substrate to form a resist film (hereinafter may be referred to as "step (1)"), (2) exposing the resist film by applying radiation to the resist film via a photomask (hereinafter may be referred to as "step (2)"), (3) heating the exposed resist film (hereinafter may be referred to as "step (3)"), and (4) developing the heated resist film (hereinafter may be referred to as "step (4)"). Each step is described in detail below.

Step (1)

In the step (1), the photoresist composition according to one embodiment of the invention is applied to a substrate to form a resist film. A silicon wafer, an aluminum-coated wafer, or the like may be used as the substrate. An organic or inorganic antireflective film as disclosed in Japanese Patent Publication (KOKOKU) No. 6-12452, Japanese Patent Application Publication (KOKAI) No. 59-93448, or the like may be formed on the substrate.

The photoresist composition may be applied by spin coating, cast coating, roll coating, or the like. The thickness of the resist film is normally 0.01 to 1 µm, and preferably 0.01 to 0.5 µm.

The resist film formed by applying the photoresist composition may optionally be prebaked (PB) to vaporize the solvent. The PB temperature is appropriately selected depending on the composition of the photoresist composition, but is normally about 30 to 200° C., and preferably 50 to 150° C.

A protective film as disclosed in Japanese Patent Application Publication (KOKAI) No. 5-188598 or the like may be formed on the resist layer in order to prevent the effects of basic impurities and the like contained in the environmental atmosphere. In order to prevent outflow (elution) of the acid generator and the like from the resist layer, a liquid immersion lithography protective film as disclosed in Japanese Patent Application Publication (KOKAI) No. 2005-352384 or the like may also be formed on the resist layer. These techniques may be used in combination.

Step (2)

In the step (2), the desired area of the resist film formed by the step (1) is subjected to reduced projection exposure via a mask having a specific pattern and an optional immersion liquid. For example, the desired area of the resist film may be subjected to reduced projection exposure via an isolated line pattern mask to form an isolated trench pattern. The resist film may be exposed a plurality of times using the desired pattern mask and another pattern mask. In this case, it is preferable to continuously (successively) expose the resist film. For example, the desired area of the resist film may be subjected to first reduced projection exposure via a line-and-space pattern mask, and then subjected to second reduced projection exposure so that the exposed areas (lines) intersect. It is preferable that the area subjected to the first reduced projection exposure perpendicularly intersect the area subjected to the second reduced projection exposure.

This makes it easy to form a circular contact hole pattern in the unexposed area enclosed by the exposed area. Examples of the immersion liquid used for exposure include water, a fluorine-containing inert liquid, and the like. It is preferable that the immersion liquid be transparent to the exposure wavelength, and have a temperature coefficient of the refractive index as small as possible so that distortion of an optical image projected onto the film is minimized. When using an ArF excimer laser (wavelength: 193 nm) as the exposure light source, it is preferable to use water from the viewpoint of availability and ease of handling.

When using water as the immersion liquid, a small amount of an additive that decreases the surface tension of water and increases the surface activity of water may be added to the water. It is preferable that the additive does not dissolve the resist layer formed on the wafer, and does not affect the optical coating of the bottom surface of the lens. Distilled water is preferably used as the water.

Radiation used for exposure is appropriately selected from ultraviolet rays, deep ultraviolet rays, X-rays, charged particle rays, and the like depending on the type of the acid generator (B). It is preferable to use deep ultraviolet rays such as ArF excimer laser light or KrF excimer laser light (wavelength: 248 nm). It is more preferable to use ArF excimer laser light. The exposure conditions (e.g., dose) are appropriately selected depending on the composition of the photoresist composition, the type of additive, and the like. The resist pattern-forming method according to one embodiment of the invention may include a plurality of exposure steps. An identical or different light source may be used in each exposure step. Note that it is preferable to use ArF excimer laser light in the first exposure step.

Step (3)

In the step (3), the exposed resist film is subjected to post-exposure bake (PEB). The acid-labile group included in the photoresist composition dissociates smoothly due to PEB. The PEB temperature is normally 30 to 200° C., and preferably 50 to 150° C. If the PEB temperature is less than 30° C., the acid-labile group may not dissociate smoothly. If the PEB temperature is 200° C. or more, an acid generated by the acid generator (B) may be diffused to the unexposed area, so that an excellent pattern may not be obtained.

Step (4)

In the step (4), the heated photoresist film is developed using a developer to form a given photoresist pattern. After development, the photoresist film (pattern) is normally rinsed with water, and dried. An alkaline aqueous solution prepared by dissolving at least one alkaline compound (e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, or 1,5-diazabicyclo-[4.3.0]-5-nonene) in water is preferably used as the developer.

Examples of the development method include a dipping method that immerses the substrate in a container filled with the developer for a given time, a puddle method that allows the developer to be present on the surface of the substrate for a given time due to surface tension, a spray method that sprays the developer onto the surface of the substrate, a dynamic dispensing method that applies the developer to the substrate that is rotated at a constant speed while scanning with a developer application nozzle at a constant speed, and the like.

Polymer

A polymer according to one embodiment of the invention includes the structural unit (I) shown by the formula (1). A photoresist composition that includes the polymer exhibits sufficient basic properties (e.g., sensitivity), and exhibits improved lithographic performance (e.g., MEEF and LWR). The detailed description of the polymer (A) included in the photoresist composition is applied to the polymer according to one embodiment of the invention. Therefore, detailed description of the polymer according to one embodiment of the invention is omitted.

Compound

A compound according to one embodiment of the invention is shown by the formula (i). Since the compound according to one embodiment of the invention has the structure shown by the formula (i), the compound may suitably be used as a monomer compound for incorporating the structural unit (I) in a polymer. The detailed description of the structural unit (I) included in the polymer (A) included in the photoresist composition is applied to the compound according to one embodiment of the invention. Therefore, detailed description of the compound according to one embodiment of the invention is omitted.

EXAMPLES

The invention is further described below by way of examples. Note that the invention is not limited to the following examples.

The Mw and the Mn of the polymer were determined under the following conditions using GPC columns manufactured by Tosoh Corporation (G2000HXL×2, G3000HXL×1, G4000HXL×1).

Column temperature: 40° C.

Eluant: tetrahydrofuran (manufactured by Wako Pure Chemical Industries, Ltd.)

Flow rate: 1.0 ml/min

Sample concentration: 1.0 mass %

Sample injection amount: 100 μl

Detector: differential refractometer

Standard: monodisperse polystyrene

The polymer was subjected to $^1$H-NMR analysis and $^{13}$C-NMR analysis using a nuclear magnetic resonance spectrometer ("JNM-EX270" manufactured by JEOL Ltd.).

Synthesis of Compound

Example 1

Synthesis of Compound (M-1)

A reactor (1 liter) equipped with a stirrer and a dropping funnel was charged with 30 g (240 mmol) of 2-bromoethanol and 200 ml of tetrahydrofuran (THF). A solution prepared by dissolving 39.8 g (264 mmol) of t-butyldimethylsilyl chloride in 100 ml of THF was poured into the dropping funnel, and added dropwise to the mixture under a nitrogen atmosphere. The mixture was reacted at 0° C. for 3 hours with stirring. The resulting suspension was filtered, and the filtrate was concentrated under reduced pressure. The residue was purified by distillation under reduced pressure to obtain 48.6 g of the compound shown by the following formula (m-1) (yield: 85%).

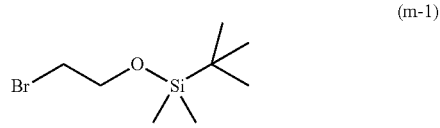

(m-1)

A reactor (1 liter) equipped with a stirrer and a dropping funnel was charged with 7.4 g (300 mmol) of magnesium and 50 ml of diethyl ether. A solution prepared by dissolving 23.9 g (200 mmol) of the compound shown by the formula (m-1) in 150 ml of diethyl ether was poured into the dropping funnel, and added dropwise to the mixture under a nitrogen atmosphere. The mixture was reacted at room temperature for 1 hour with stirring. A solution prepared by dissolving 12.6 g (150 mmol) of cyclopentanone in 100 ml of diethyl ether was added dropwise to the mixture from the dropping funnel, and the mixture was reacted for 3 hours with stirring. After cooling the mixture with ice, 15.2 g (150 mmol) of triethylamine was added to the mixture. After the addition of a solution prepared by dissolving 11.5 g (110 mmol) of methacrylic chloride in 30 ml of THF, the mixture was reacted for 6 hours. After completion of the reaction, the resulting suspension was concentrated under reduced pressure, and the residue was purified by silica gel column chromatography (eluant: hexane/ethyl acetate (=5/1)) to obtain 31.8 g of the compound shown by the following formula (m-2) (yield: 65%).

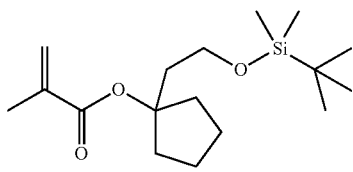

(m-2)

A reactor (1 liter) equipped with a stirrer and a dropping funnel was charged with 24.5 g (100 mmol) of the compound shown by the formula (m-2) and 120 ml of THF. A solution prepared by dissolving 32.7 g (125 mmol) of tetrabutylammonium fluoride in 30 ml of THF was poured into the dropping funnel, and added dropwise to the mixture under a nitrogen atmosphere. The mixture was reacted at room temperature for 3 hours with stirring. After completion of the reaction, ethyl acetate was added to the mixture. The mixture was washed with a sodium hydroxide aqueous solution, and concentrated under reduced pressure. The residue was purified by silica gel column chromatography (eluant: hexane/ethyl acetate (=4/1)) to obtain 15.9 g of the compound shown by the following formula (M-1) (compound (M-1)) (yield: 80%).

The $^1$H-NMR data for the compound (M-1) is shown below.

$^1$H-NMR (CDCl$_3$) δ: 1.41 (t, 2H, CH$_2$), 1.45 (m, 4H, CH$_2$), 1.71 (t, 3H, CH$_3$), 1.93 (m, 4H, CH$_2$), 2.50 (br, 1H, OH), 3.41 (t, 2H, CH$_2$), 5.37 (s, 1H, CH), 5.98 (s, 1H, CH).

Example 2

Synthesis of Compound (M-2)

22.0 g of the compound shown by the following formula (M-2) (compound (M-2)) was obtained in the same manner as in Example 1, except that 18.9 g (150 mmol) of cyclooctanone was used instead of 12.6 g of cyclopentanone (yield: 62%).

The $^1$H-NMR data for the compound (M-2) is shown below.

$^1$H-NMR (CDCl$_3$) δ: 1.38-2.03 (m, 23H, CH$_2$, CH$_3$), 2.46 (br, 1H, OH), 3.38 (t, 2H, CH$_2$), 5.36 (s, 1H, CH), 5.96 (s, 1H, CH).

Example 3

Synthesis of Compound (M-3)

23.4 g of the compound shown by the following formula (M-3) (compound (M-3)) was obtained in the same manner as in Example 1, except that 22.5 g (150 mmol) of 2-adamantanone was used instead of 12.6 g of cyclopentanone (yield: 59%).

The $^1$H-NMR data for the compound (M-3) is shown below.

$^1$H-NMR (CDCl$_3$) δ: 1.25-2.24 (m, 23H, CH, CH$_2$, CH$_3$), 2.54 (br, 1H, OH), 3.40 (t, 2H, CH$_2$), 5.37 (s, 1H, CH), 5.89 (s, 1H, CH).

Example 4

Synthesis of Compound (M-4)

31.1 g of the compound shown by the following formula (M-4) (compound (M-4)) was obtained in the same manner as in Example 1, except that 33.4 g (240 mmol) of 1-bromo-2-propanol was used instead of 30 g of 2-bromoethanol (yield: 61%).

The $^1$H-NMR data for the compound (M-4) is shown below.

$^1$H-NMR (CDCl$_3$) δ: 1.40 (t, 2H, CH$_2$), 1.45 (m, 4H, CH$_2$), 1.59 (s, 3H, CH$_3$), 1.71 (t, 3H, CH$_3$), 1.94 (m, 4H, CH$_2$), 2.48 (br, 1H, OH), 3.41 (t, 2H, CH$_2$), 5.37 (s, 1H, CH), 5.89 (s, 1H, CH).

Example 5

Synthesis of Compound (M-5)

31.5 g of the compound shown by the following formula (M-5) (compound (M-5)) was obtained in the same manner as in Example 1, except that 36.7 g (240 mmol) of 4-bromo-1-butanol was used instead of 30 g of 2-bromoethanol (yield: 58%).

The $^1$H-NMR data for the compound (M-5) is shown below.

$^1$H-NMR (CDCl$_3$) δ: 1.37 (t, 2H, CH$_2$), 1.42-1.52 (m, 8H, CH$_2$), 1.72 (t, 3H, CH$_3$), 1.93 (m, 4H, CH$_2$), 2.49 (br, 1H, OH), 3.42 (t, 2H, CH$_2$), 5.36 (s, 1H, CH), 5.90 (s, 1H, CH).

Example 6

A reactor (1 liter) equipped with a stirrer and a dropping funnel was charged with 28.8 g (150 mmol) of 4-bromo-1-butanol (manufactured by Tokyo Chemical Industry Co., Ltd., purity: 80%), 0.25 g (1.5 mmol) of tosylic acid, and 300 ml of dichloromethane. The mixture was reacted at room temperature for 6 hours with stirring under a nitrogen atmosphere. The resulting suspension was filtered, and the filtrate was concentrated under reduced pressure. The residue was purified by distillation under reduced pressure to obtain 29.5 g of the compound shown by the following formula (m-3) (yield: 83%).

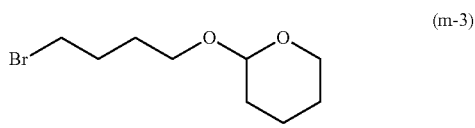 [SMILES: BrCCCCOC1CCCCO1]

(m-3)

A reactor (1 liter) equipped with a stirrer and a dropping funnel was charged with 9.4 g (340 mmol) of magnesium and 50 ml of diethyl ether. A solution prepared by dissolving 30.8 g (130 mmol) of the compound shown by the formula (m-3) in 150 ml of diethyl ether was poured into the dropping funnel, and added dropwise to the mixture under a nitrogen atmosphere. The mixture was reacted at room temperature for 1 hour with stirring. A solution prepared by dissolving 16.4 g (195 mmol) of cyclopentanone in 100 ml of diethyl ether was added dropwise to the mixture from the dropping funnel, and the mixture was reacted for 3 hours with stirring. After cooling the mixture with ice, 17.2 g (170 mmol) of triethylamine was added to the mixture. After the addition of a solution prepared by dissolving 11.5 g (71.5 mmol) of methacrylic chloride in 30 ml of THF, the mixture was reacted for 6 hours. After completion of the reaction, the resulting suspension was concentrated under reduced pressure, and the residue was purified by silica gel column chromatography (eluant: hexane/ethyl acetate (=5/1)) to obtain 39.5 g of the compound shown by the following formula (M-6) (compound (M-6)) (yield: 68%).

The $^1$H-NMR data for the compound (M-6) is shown below.

$^1$H-NMR (CDCl$_3$) δ: 1.28-1.59 (m, 16H, CH$_2$), 1.70 (s, 3H, CH$_3$), 1.92 (m, 2H, CH$_2$), 2.07 (m, 2H, CH$_2$), 3.26-3.40 (m, 2H, CH$_2$), 3.60-3.74 (m, 2H, CH$_2$), 4.48 (s, 1H, CH), 5.36 (s, 1H, CH), 5.90 (s, 1H, CH).

Example 7

8.89 g of the compound shown by the following formula (M-7) (compound (M-7)) was obtained in the same manner as in Example 6, except that 18.7 g (150 mmol) of 2-bromo-1-ethanol was used instead of 28.8 g of 4-bromo-1-butanol (yield: 21%).

The $^1$H-NMR data for the compound (M-7) is shown below.

$^1$H-NMR (CDCl$_3$) δ: 1.29-1.56 (m, 12H, CH$_2$), 1.69 (s, 3H, CH$_3$), 1.92 (m, 2H, CH$_2$), 2.08 (m, 2H, CH$_2$), 3.26-3.40 (m, 2H, CH$_2$), 3.60-3.74 (m, 2H, CH$_2$), 4.48 (s, 1H, CH), 5.36 (s, 1H, CH), 5.90 (s, 1H, CH).

Example 8

42.2 g of the compound shown by the following formula (M-8) (compound (M-8)) was obtained in the same manner as in Example 6, except that 24.6 g (195 mmol) of cyclooctanone was used instead of 16.4 g of cyclopentanone (yield: 60%).

The $^1$H-NMR data for the compound (M-8) is shown below.

$^1$H-NMR (CDCl$_3$) δ: 1.30-1.62 (m, 18H, CH$_2$), 1.69 (s, 3H, CH$_3$), 1.92-2.08 (m, 8H, CH$_2$), 3.26-3.40 (m, 2H, CH$_2$), 3.60-3.74 (m, 2H, CH$_2$), 4.48 (s, 1H, CH), 5.36 (s, 1H, CH), 5.90 (s, 1H, CH).

Example 9

41.1 g of the compound shown by the following formula (M-9) (compound (M-9)) was obtained in the same manner as in Example 6, except that 29.3 g (195 mmol) of 2-adamantanone was used instead of 16.4 g of cyclopentanone (yield: 56%).

The $^1$H-NMR data for the compound (M-9) is shown below.

$^1$H-NMR (CDCl$_3$) δ: 1.22-2.50 (m, 30H, CH$_2$, CH$_3$), 3.60 (t, 2H, CH$_2$), 3.73 (t, 2H, CH$_2$), 5.37 (s, 1H, CH), 5.89 (s, 1H, CH).

Synthesis of Polymer (A)

The monomers shown by the following formulas (M-1) to (M-16) were used to synthesize a polymer (A).

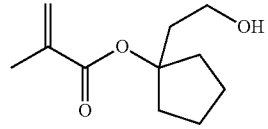
(M-1)

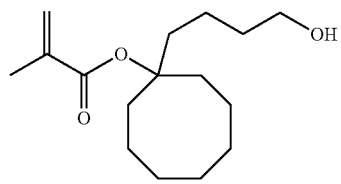
(M-2)

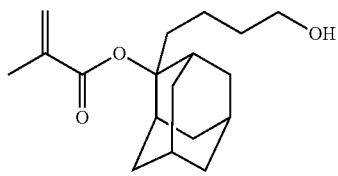
(M-3)

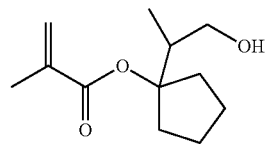
(M-4)

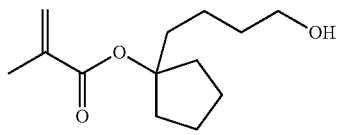
(M-5)

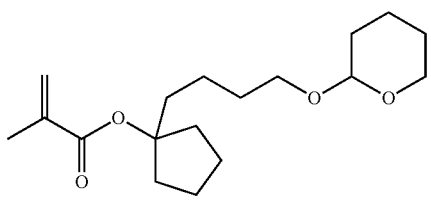
(M-6)

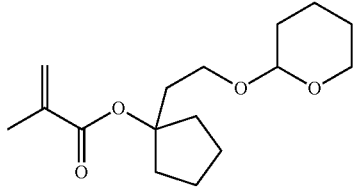
(M-7)

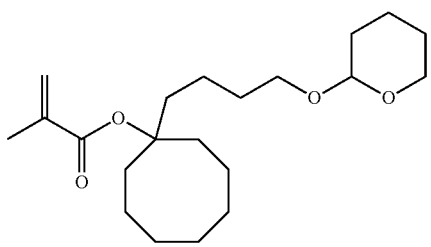
(M-8)

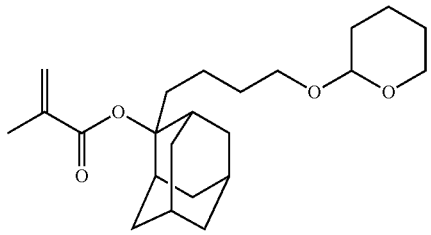
(M-9)

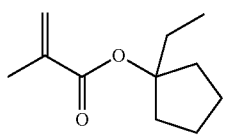
(M-10)

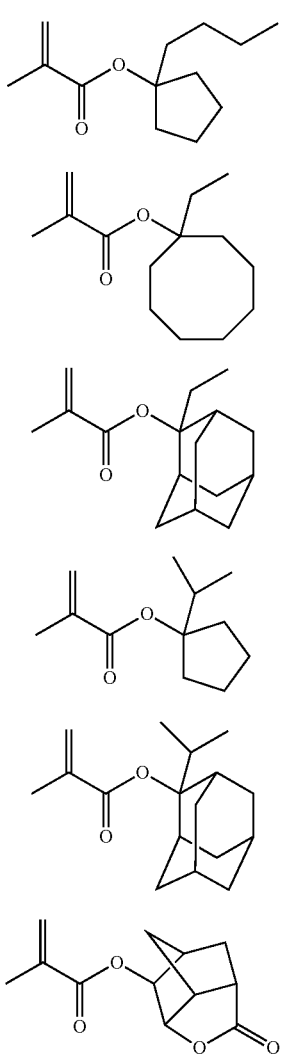

Example 10

13.6 g (50 mol %) of the compound (M-1) and 16.4 g (50 mol %) of the compound (M-16) were dissolved in 60 g of 2-butanone, and 1.21 g of AIBN was added to the solution to prepare a monomer solution. A three-necked flask (500 ml) was charged with 30 g of 2-butanone, purged with nitrogen for 30 minutes, and heated to 80° C. with stirring. The monomer solution was added dropwise to the flask using a dropping funnel over 3 hours. The monomers were polymerized for 6 hours from the start of addition of the monomer solution. After completion of polymerization, the polymer solution was cooled with water to 30° C. or less. The cooled polymer solution was added to 600 g of methanol, and a white powder that precipitated by this operation was filtered off. The white powder was washed twice with 120 g of methanol, filtered off, and dried at 50° C. for 17 hours to obtain a white powdery polymer (A-1) (24.6 g, yield: 82%). The polymer (A-1) had an Mw of 5000 and a dispersity (Mw/Mn) of 1.31. The content of low-molecular-weight components in the polymer (A-1) was 0.05%. The ratio of structural units derived from the compound (M-1) to structural units derived from the compound (M-16) in the polymer (A-1) determined by $^{13}$C-NMR analysis was 48:52 (mol %).

Examples 11 to 21 and Synthesis Examples 1 to 5

Polymers (A-2) to (A-12) and (a-1) to (a-5) were obtained in the same manner as in Example 10, except for using the monomers shown in Table 1 in a given ratio. The Mw, the dispersity (Mw/Mn), and the yield (%) of each polymer, and the content of structural units derived from each monomer in each polymer are also shown in Table 1.

TABLE 1

| | | Monomer | | Structural unit | Property value | | |
|---|---|---|---|---|---|---|---|
| | Polymer | Type | Amount (mol %) | content (mol %) | Yield (%) | Mw | Mw/Mn |
| Example 10 | A-1 | M-1 | 50 | 48 | 82.0 | 5000 | 1.31 |
| | | M-16 | 50 | 52 | | | |
| Example 11 | A-2 | M-1 | 40 | 39 | 76.0 | 4900 | 1.32 |
| | | M-13 | 10 | 9 | | | |
| | | M-16 | 50 | 52 | | | |
| Example 12 | A-3 | M-2 | 40 | 38 | 77.0 | 5000 | 1.34 |
| | | M-13 | 10 | 9 | | | |
| | | M-16 | 50 | 53 | | | |
| Example 13 | A-4 | M-4 | 40 | 38 | 78.0 | 5000 | 1.31 |
| | | M-15 | 10 | 9 | | | |
| | | M-16 | 50 | 53 | | | |
| Example 14 | A-5 | M-5 | 40 | 38 | 84.0 | 5100 | 1.31 |
| | | M-15 | 10 | 8 | | | |
| | | M-16 | 50 | 54 | | | |
| Example 15 | A-6 | M-1 | 40 | 48 | 79.0 | 5000 | 1.32 |
| | | M-3 | 10 | 8 | | | |
| | | M-16 | 50 | 54 | | | |
| Example 16 | A-7 | M-7 | 50 | 48 | 77.0 | 5100 | 1.33 |
| | | M-16 | 50 | 52 | | | |
| Example 17 | A-8 | M-6 | 50 | 48 | 75.0 | 5100 | 1.34 |
| | | M-16 | 50 | 52 | | | |
| Example 18 | A-9 | M-8 | 50 | 49 | 74.0 | 5100 | 1.35 |
| | | M-16 | 50 | 51 | | | |
| Example 19 | A-10 | M-1 | 40 | 38 | 76.0 | 4900 | 1.31 |
| | | M-9 | 10 | 8 | | | |
| | | M-16 | 50 | 54 | | | |
| Example 20 | A-11 | M-7 | 10 | 38 | 75.0 | 5000 | 1.33 |
| | | M-11 | 40 | 9 | | | |
| | | M-16 | 50 | 53 | | | |
| Example 21 | A-12 | M-9 | 20 | 39 | 77.0 | 5100 | 1.34 |
| | | M-10 | 40 | 18 | | | |
| | | M-16 | 40 | 43 | | | |
| Synthesis Example 1 | a-1 | M-10 | 50 | 49 | 80.0 | 5100 | 1.35 |
| | | M-16 | 50 | 51 | | | |
| Synthesis Example 2 | a-2 | M-10 | 40 | 39 | 78.0 | 5000 | 1.33 |
| | | M-13 | 10 | 9 | | | |
| | | M-16 | 50 | 52 | | | |
| Synthesis Example 3 | a-3 | M-12 | 40 | 39 | 80.0 | 4900 | 1.32 |
| | | M-13 | 10 | 9 | | | |
| | | M-16 | 50 | 52 | | | |
| Synthesis Example 4 | a-4 | M-14 | 40 | 38 | 83.0 | 5000 | 1.33 |
| | | M-15 | 10 | 8 | | | |
| | | M-16 | 50 | 54 | | | |
| Synthesis Example 5 | a-5 | M-11 | 40 | 38 | 80.0 | 5100 | 1.31 |
| | | M-15 | 10 | 8 | | | |
| | | M-16 | 50 | 54 | | | |

Preparation of Photoresist Composition

The following acid generator (B), compound (C), and solvent were used to prepare a photoresist composition.

Acid Generator (B)

Compounds shown by the following formulas (B-1) to (B-3)

Compound (C)

Compound shown by the following formula (C-1)

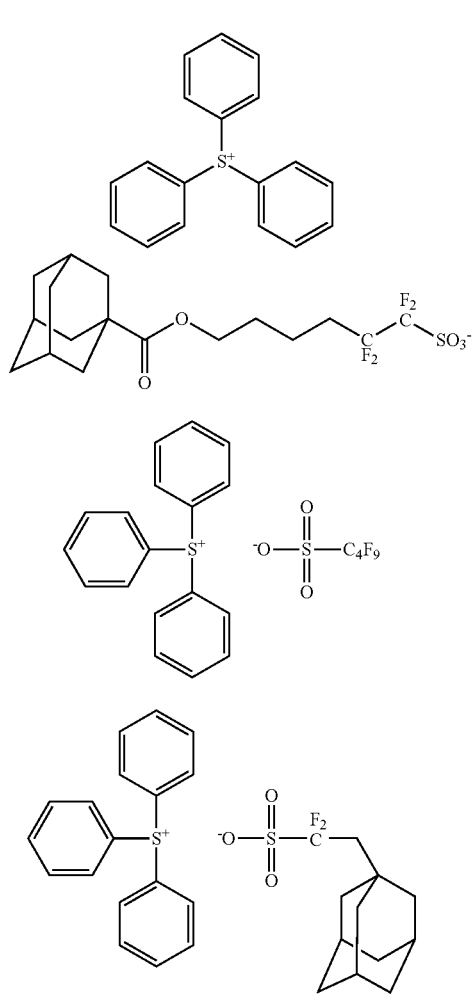

Solvent

The following solvents were used in the examples and comparative examples.

(D-1): propylene glycol monomethyl ether acetate (D-2): cyclohexanone (D-3): γ-butyrolactone Example 22

100 parts by mass of the polymer (A-1) (polymer (A)), 10.8 parts by mass of the acid generator (B-1) (acid generator (B)), 6.7 parts by mass of the compound (C-1) (compound (C)), 2590 parts by mass of the solvent (D-1), 1110 parts by mass of the solvent (D-2), and 200 parts by mass of the solvent (D-3) were mixed. The mixture was filtered through a filter having a pore size of 0.20 μm to prepare a photoresist composition.

Examples 23 to 36 and Comparative Examples 1 to 5

A photoresist composition was prepared in the same manner as in Example 22, except that the composition was changed as shown in Table 2.

TABLE 2

| | Component (A) | | Acid generator (B) | | Compound (C) | | Baking temperature (° C.) | | MEEF | Sensitivity (mJ/cm$^2$) | LWR (nm) |
|---|---|---|---|---|---|---|---|---|---|---|---|
| | Type | Parts by mass | Type | Parts by mass | Type | Parts by mass | SB | PEB | | | |
| Example 22 | A-1 | 100 | B-1 | 10.8 | C-1 | 6.7 | 100.0 | 100.0 | 3.3 | 37 | 5.3 |
| Example 23 | A-2 | 100 | B-1 | 10.8 | C-1 | 6.7 | 100.0 | 100.0 | 3.2 | 35 | 5.2 |
| Example 24 | A-3 | 100 | B-1 | 10.8 | C-1 | 6.7 | 100.0 | 90.0 | 3.3 | 33 | 5.3 |
| Example 25 | A-4 | 100 | B-1 | 10.8 | C-1 | 6.7 | 100.0 | 90.0 | 3.4 | 33 | 5.3 |
| Example 26 | A-5 | 100 | B-1 | 10.8 | C-1 | 6.7 | 100.0 | 90.0 | 3.2 | 33 | 5.2 |
| Example 27 | A-6 | 100 | B-1 | 10.8 | C-1 | 6.7 | 100.0 | 90.0 | 3.3 | 33 | 5.2 |
| Example 28 | A-7 | 100 | B-1 | 10.8 | C-1 | 6.7 | 100.0 | 90.0 | 3.6 | 34 | 5.3 |
| Example 29 | A-8 | 100 | B-1 | 10.8 | C-1 | 6.7 | 100.0 | 100.0 | 3.2 | 35 | 5.1 |
| Example 30 | A-9 | 100 | B-1 | 10.8 | C-1 | 6.7 | 100.0 | 100.0 | 3.2 | 34 | 5.2 |
| Example 31 | A-10 | 100 | B-1 | 10.8 | C-1 | 6.7 | 100.0 | 100.0 | 3.3 | 33 | 5.2 |
| Example 32 | A-11 | 100 | B-1 | 10.8 | C-1 | 6.7 | 100.0 | 100.0 | 3.1 | 35 | 5.1 |
| Example 33 | A-12 | 100 | B-1 | 10.8 | C-1 | 6.7 | 100.0 | 100.0 | 3.2 | 33 | 5.2 |
| Example 34 | A-8 | 100 | B-2 | 10.8 | C-1 | 6.7 | 100.0 | 100.0 | 3.3 | 33 | 5.0 |
| Example 35 | A-9 | 100 | B-2 | 10.8 | C-1 | 6.7 | 100.0 | 100.0 | 3.1 | 32 | 5.1 |
| Example 36 | A-8 | 100 | B-3 | 10.8 | C-1 | 6.7 | 100.0 | 100.0 | 3.2 | 37 | 5.2 |
| Comparative Example 1 | a-1 | 100 | B-1 | 10.8 | C-1 | 6.7 | 100.0 | 90.0 | 3.7 | 35 | 5.6 |
| Comparative Example 2 | a-2 | 100 | B-1 | 10.8 | C-1 | 6.7 | 100.0 | 100.0 | 3.7 | 35 | 5.8 |

TABLE 2-continued

| | Component (A) | | Acid generator (B) | | Compound (C) | | Baking temperature (° C.) | | MEEF | Sensitivity (mJ/cm$^2$) | LWR (nm) |
|---|---|---|---|---|---|---|---|---|---|---|---|
| | Type | Parts by mass | Type | Parts by mass | Type | Parts by mass | SB | PEB | | | |
| Comparative Example 3 | a-3 | 100 | B-1 | 10.8 | C-1 | 6.7 | 100.0 | 100.0 | 3.6 | 34 | 5.7 |
| Comparative Example 4 | a-4 | 100 | B-1 | 10.8 | C-1 | 6.7 | 100.0 | 90.0 | 3.7 | 32 | 5.9 |
| Comparative Example 5 | a-5 | 100 | B-1 | 10.8 | C-1 | 6.7 | 100.0 | 90.0 | 3.7 | 33 | 5.9 |

Evaluation

The photoresist composition was evaluated as described below. The results are shown in Table 2.

Evaluation of Sensitivity

A film (thickness: 75 nm) of the photoresist composition was formed on a 12-inch silicon wafer on which an underlayer antireflective film ("ARC66" manufactured by Nissan Chemical Industries, Ltd.) was formed. The film was then soft-baked (SB) at 100° C. for 60 seconds. The film was then exposed via a mask pattern for forming a 50 nm line/100 nm pitch pattern using an ArF immersion scanner ("NSR S610C" manufactured by Nikon Corporation) (NA=1.3, ratio=0.800, Annular). The exposed film was subjected to post-exposure bake (PEB) at 100° C. for 60 seconds. The film was then developed using a 2.38 mass % tetramethylammonium hydroxide aqueous solution, rinsed with water, and dried to form a positive-tone resist pattern. A dose at which the area exposed via the mask pattern for forming a 50 nm line/100 nm pitch pattern formed a line having a line width of 50 nm was determined to be an optimum dose (Eop). The optimum dose was taken as the sensitivity (mJ/cm$^2$). The measurement was performed using a scanning electron microscope ("CG4000" manufactured by Hitachi High-Technologies Corporation).

A case where the sensitivity was 40 mJ/cm$^2$ or less was evaluated as acceptable.

Mask Error Enhancement Factor (MEEF)

An LS pattern (pitch: 100 nm) was formed using the photoresist composition at the optimum dose (Eop) determined when evaluating the sensitivity via a 42 nm line/58 nm pitch mask pattern, a 46 nm line/54 nm pitch mask pattern, or a 50 nm line/100 nm pitch mask pattern. A graph was drawn by plotting the mask line size (nm) (horizontal axis) and the line width (nm) of the resist film formed using each mask pattern (vertical axis), and the slope of the straight line of the graph was calculated to be the MEEF. The MEEF (i.e., the slope of the straight line) becomes closer to 1 as the mask reproducibility increases.

Line Width Roughness (LWR)

A positive-tone resist pattern was formed, and the optimum dose (Eop) was determined in the same manner as described above (see "Evaluation of sensitivity"). The line (width: 50 nm) of the resist pattern formed at the optimum dose (Eop) was observed from above using a scanning electron microscope ("S9220" manufactured by Hitachi Ltd.), and the line width was measured at an arbitrary 10 points. The 3σ value (variation) of the line width measured values was evaluated as the LWR (nm). It was determined that an excellent pattern shape was obtained when the LWR was 5.4 nm or less.

As shown in Table 2, it was confirmed that the photoresist compositions according to the embodiments of the invention exhibited sufficient sensitivity, and exhibited excellent lithographic performance (i.e., small MEEF and small LWR).

The photoresist compositions according to the embodiments of the invention may suitably be used to form a resist pattern in a lithographic process employed when producing various electronic devices (e.g., semiconductor devices and liquid crystal devices).

Obviously, numerous modifications and variations of the invention are possible in light of the above teachings. It is therefore to be understood that within the scope of the appended claims, the invention may be practiced otherwise than as specifically described herein.

What is claimed is:

1. A resist pattern-forming method comprising:
applying a photoresist composition to a substrate to form a resist film;
exposing the resist film by applying radiation to the resist film via a photomask;
heating the exposed resist film;
developing the heated resist film; and
rinsing and drying the developed resist film to form a resist pattern made from the photoresist composition,
wherein the photoresist composition comprises:
a polymer that includes a structural unit shown by a formula (1); and
a photoacid generator,

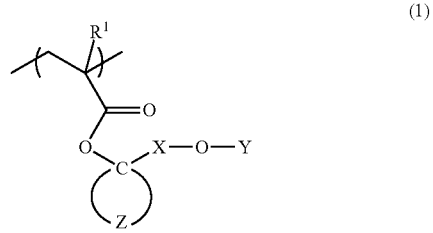

wherein $R^1$ represents a hydrogen atom, a fluorine atom, a methyl group, or a trifluoromethyl group, Z represents a group that forms a divalent monoalicyclic group having 5 to 8 carbon atoms together with a carbon atom bonded to X, X represents an alkanediyl group having 1 to 6 carbon atoms, Y represents a hydrogen atom or —$CR^2R^3(OR^4)$, and $R^2$ to $R^4$ independently represent a hydrogen atom or a monovalent hydrocarbon group, provided that $R^3$ and $R^4$ optionally bond to each other to form a cyclic ether structure together with a carbon atom bonded to $R^3$ and an oxygen atom bonded to $R^4$.

2. The resist pattern-forming method according to claim 1, wherein X represents an alkanediyl group having 2 to 4 carbon atoms.

3. The resist pattern-forming method according to claim 1, wherein Y represents —$CR^2R^3(OR^4)$.

4. The resist pattern-forming method according to claim 1, wherein the polymer further includes a structural unit shown by a formula (2),

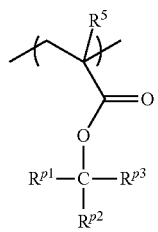
(2)

wherein $R^5$ represents a hydrogen atom, a fluorine atom, a methyl group, or a trifluoromethyl group, $R^{p1}$ represents a chain-like hydrocarbon group having 1 to 10 carbon atoms or an alicyclic group having 3 to 20 carbon atoms, and $R^{p2}$ and $R^{p3}$ independently represent a chain-like hydrocarbon group having 1 to 10 carbon atoms or an alicyclic group having 4 to 20 carbon atoms, provided that $R^{p2}$ and $R^{p3}$ optionally bond to each other to form a divalent alicyclic group having 4 to 20 carbon atoms together with a carbon atom bonded to $R^{p2}$ and $R^{p3}$.

5. The resist pattern-forming method according to claim 1, wherein the photoresist composition further comprises either or both of a compound shown by a formula (3-1) and a compound shown by a formula (3-2),

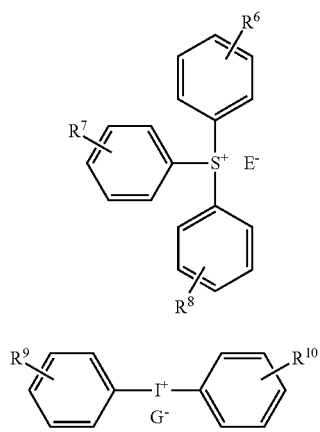
(3-1)

(3-2)

wherein $R^6$ to $R^{10}$ independently represent a hydrogen atom, an alkyl group, an alkoxy group, a hydroxyl group, or a halogen atom, $E^-$ and $G^-$ independently represent $OH^{31}$, $R^A$—COO$^-$, $R^A$—SO$_3^-$, or $R^A$—N$^-$—SO$_2$—$R^B$, $R^A$ represents an alkyl group, a cycloalkyl group, an aryl group, or an aralkyl group, provided that some or all of hydrogen atoms included in $R^A$ may be substituted with a substituent, and $R^B$ represents an alkyl group or an aralkyl group, provided that some or all of hydrogen atoms included in $R^B$ may be substituted with a fluorine atom.

6. A photoresist composition comprising a polymer that includes a structural unit shown by a formula (1), and a photoacid generator,

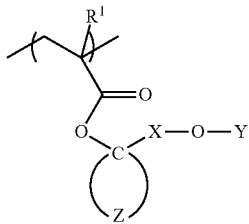
(1)

wherein $R^1$ represents a hydrogen atom, a fluorine atom, a methyl group, or a trifluoromethyl group, Z represents a group that forms a divalent alicyclic group having 3 to 20 carbon atoms together with a carbon atom bonded to X, X represents an alkanediyl group having 1 to 6 carbon atoms, Y represents —CR$^2$R$^3$(OR$^4$), and $R^2$ to $R^4$ independently represent a hydrogen atom or a monovalent hydrocarbon group, provided that $R^3$ and $R^4$ optionally bond to each other to form a cyclic ether structure together with a carbon atom bonded to $R^3$ and an oxygen atom bonded to $R^4$.

7. The photoresist composition according to claim 6, wherein X represents an alkanediyl group having 2 to 4 carbon atoms.

8. The photoresist composition according to claim 6, wherein the polymer further includes a structural unit shown by a formula (2),

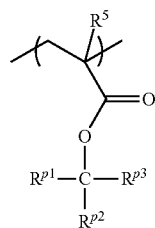
(2)

wherein $R^5$ represents a hydrogen atom, a fluorine atom, a methyl group, or a trifluoromethyl group, $R^{p1}$ represents a chain-like hydrocarbon group having 1 to 10 carbon atoms or an alicyclic group having 3 to 20 carbon atoms, and $R^{p2}$ and $R^{p3}$ independently represent a chain-like hydrocarbon group having 1 to 10 carbon atoms or an alicyclic group having 4 to 20 carbon atoms, provided that $R^{p2}$ and $R^{p3}$ optionally bond to each other to form a divalent alicyclic group having 4 to 20 carbon atoms together with a carbon atom bonded to $R^{p2}$ and $R^{p3}$.

9. The photoresist composition according to claim 6, further comprising either or both of a compound shown by a formula (3-1) and a compound shown by a formula (3-2),

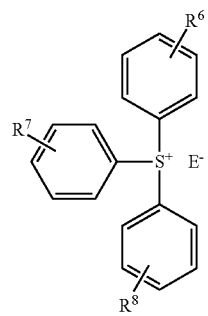
(3-1)

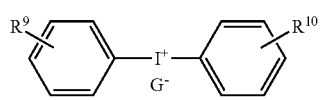
(3-2)

wherein $R^6$ to $R^{10}$ independently represent a hydrogen atom, an alkyl group, an alkoxy group, a hydroxyl group, or a halogen atom, $E^-$ and $G^-$ independently represent $OH^-$, $R^A$—$COO^-$, $R^A$—$SO_3^-$, or $R^A$—$N^-$—$SO_2$—$R^B$, $R^A$ represents an alkyl group, a cycloalkyl group, an aryl group, or an aralkyl group, provided that some or all of hydrogen atoms included in $R^A$ may be substituted with a substituent, and $R^B$ represents an alkyl group or an aralkyl group, provided that some or all of hydrogen atoms included in $R^B$ may be substituted with a fluorine atom.

10. A resist pattern-forming method comprising applying the photoresist composition according to claim 6 to a substrate to form a resist film, exposing the resist film by applying radiation to the resist film via a photomask, heating the exposed resist film, and developing the heated resist film.

11. A polymer comprising a structural unit shown by a formula (1),

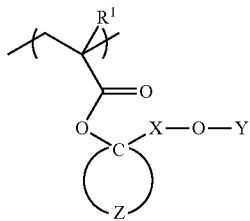
(1)

wherein $R^1$ represents a hydrogen atom, a fluorine atom, a methyl group, or a trifluoromethyl group, Z represents a group that forms a divalent alicyclic group having 3 to 20 carbon atoms together with a carbon atom bonded to X, X represents an alkanediyl group having 1 to 6 carbon atoms, Y represents —$CR^2R^3(OR^4)$, and $R^2$ to $R^4$ independently represent a hydrogen atom or a monovalent hydrocarbon group, provided that $R^3$ and $R^4$ optionally bond to each other to form a cyclic ether structure together with a carbon atom bonded to $R^3$ and an oxygen atom bonded to $R^4$.

12. A compound shown by a formula (i),

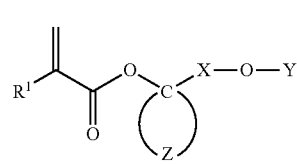
(i)

wherein $R^1$ represents a hydrogen atom, a fluorine atom, a methyl group, or a trifluoromethyl group, Z represents a group that forms a divalent alicyclic group having 3 to 20 carbon atoms together with a carbon atom bonded to X, X represents an alkanediyl group having 1 to 6 carbon atoms, Y represents —$CR^2R^3(OR^4)$, and $R^2$ to $R^4$ independently represent a hydrogen atom or a monovalent hydrocarbon group, provided that $R^3$ and $R^4$ optionally bond to each other to form a cyclic ether structure together with a carbon atom bonded to $R^3$ and an oxygen atom bonded to $R^4$.

* * * * *